US012594324B2

(12) United States Patent
Balachandran et al.

(10) Patent No.: US 12,594,324 B2
(45) Date of Patent: Apr. 7, 2026

(54) METHODS AND COMPOSITIONS FOR TREATMENT OF PANCREATIC CANCER

(71) Applicant: MEMORIAL SLOAN KETTERING CANCER CENTER, New York, NY (US)

(72) Inventors: Vinod Balachandran, New York, NY (US); Taha Merghoub, Jersey City, NJ (US); John Alec Moral, San Diego, CA (US)

( * ) Notice: Subject to any disclaimer, the term of this patent is extended or adjusted under 35 U.S.C. 154(b) by 1109 days.

(21) Appl. No.: 17/623,867

(22) PCT Filed: Jun. 30, 2020

(86) PCT No.: PCT/US2020/040262
§ 371 (c)(1),
(2) Date: Dec. 29, 2021

(87) PCT Pub. No.: WO2021/003138
PCT Pub. Date: Jan. 7, 2021

(65) Prior Publication Data
US 2022/0370562 A1 Nov. 24, 2022

Related U.S. Application Data

(60) Provisional application No. 62/937,219, filed on Nov. 18, 2019, provisional application No. 62/868,976, filed on Jun. 30, 2019.

(51) Int. Cl.
*A61K 38/20* (2006.01)
*A61K 35/12* (2015.01)
*A61K 38/00* (2006.01)
*A61K 40/10* (2025.01)
*A61K 40/19* (2025.01)
*A61K 40/24* (2025.01)
*A61K 40/42* (2025.01)
*A61P 35/00* (2006.01)

(52) U.S. Cl.
CPC .............. *A61K 38/20* (2013.01); *A61K 35/12* (2013.01); *A61K 38/005* (2013.01); *A61K 40/10* (2025.01); *A61K 40/19* (2025.01); *A61K 40/24* (2025.01); *A61K 40/428* (2025.01); *A61P 35/00* (2018.01); *A61K 2239/54* (2023.05)

(58) Field of Classification Search
None
See application file for complete search history.

(56) References Cited

U.S. PATENT DOCUMENTS

| | | |
|---|---|---|
| 2015/0202291 A1 | 7/2015 | Bosch et al. |
| 2018/0050091 A1 | 2/2018 | Jefferies |
| 2018/0128837 A1 | 5/2018 | Schmitz et al. |

FOREIGN PATENT DOCUMENTS

| | | |
|---|---|---|
| WO | 2016138590 A1 | 9/2016 |
| WO | 2018175924 A1 | 9/2018 |

OTHER PUBLICATIONS

Liew FY, Girard JP, Turnquist HR. Interleukin-33 in health and disease. Nat Rev Immunol. Nov. 2016; 16(11):676-689. (Year: 2016).*
Himli M. et al., "Immune therapies in pancreatic ductal adenocarcinoma: Where are we now?", World J Gastroenterol. May 28, 2018; 24(20):2137-2151 (Year: 2018).*
Fang Y. et al., "IL-33 acts as a foe to MIA PaCa-2 pancreatic cancer", Med Oncol. Feb. 2017;34(2):23 (Year: 2017).*
Balachandran et al., "Identification of unique neoantigen qualities in long term pancreatic cancer survivors", Author manuscript, Nov. 23, 2017, 551(7681), 34 Pages.
Fang et al., "IL-33 acts as a foe to MIA PaCa-2 pancreatic cancer", Med Oncol, published on Jan. 5, 2017, 9 Pages.
Gao et al., "Tumoral Expression of IL-33 Inhibits Tumor Growth and Modifies the Tumor Microenvironment through CD8+ T and NK Cells", The Journal of Immunology, 2014, 9 Pages.
Kieler et al., "Plasma levels of interleukin-33 and soluble suppression of tumorigenicity 2 in patients with advanced pancreatic ductal adenocarcinoma undergoing systemic chemotherapy", Medical Oncology (2019), 7 Pages.
Liew et al., "Interleukin-33 in health and disease", Nov. 2016, vol. 16, 14 Pages.
Lu et al. "Interleukin-33 in tumorigenesis, tumor immune evasion, and cancer immunotherapy", J Mol Med, Published on Feb. 27, 2016, 9 Pages.
Mallett et al., "Programmed Cell Death-1 Receptor (PD-1)-Mediated Regulation of Innate Lymphoid Cells", International Journal of Molecular Sciences, 2019, 13 Pages.
Moral et al., "ILC2s amplify PD-1 blockade by activating tissue-specific cancer immunity", Mar. 5, 2020, vol. 579, 25 Pages.
Qin et al., "Exogenous IL-33 overcomes T cell tolerance in murine acute myeloid leukemia", published on Aug. 10, 2016, vol. 7, No. 38, 12 Pages.
Saranchova et al., "Type 2 Innate Lymphocytes Actuate Immunity Against Tumours and Limit Cancer Metastasis", Scientific Reports, published on Feb. 13, 2018, 17 Pages.
Sato, "Role of ETS Family Transcription Factors in Vascular Development and Angiogenesis", Cell Structure And Function, 2001, 6 Pages.
Taylor et al., "PD-1 regulates KLRG1+ group 2 innate lymphoid cells", The Journal of Experimental Medicine, vol. 214, No. 6, 1663-1678 Pages.

(Continued)

*Primary Examiner* — Daniel E Kolker
*Assistant Examiner* — Peter Johansen
(74) *Attorney, Agent, or Firm* — Gromes & Yvon LLP

(57) ABSTRACT

The present invention provides various compositions and methods useful for the treatment of pancreatic cancer, such as pancreatic ductal adenocarcinoma (PDAC), and methods for activating pancreatic tissue-specific anti-tumor T cell immunity. In some embodiments such methods involve administration of IL33. In some embodiments such methods involve administration of a PD-1 and/or PD-L1 inhibitor.

9 Claims, 14 Drawing Sheets

Specification includes a Sequence Listing.

(56)                    References Cited

OTHER PUBLICATIONS

Beek et al., "Innate Lymphoid Cells in Tumor Immunity", Biomedicines, 2016, 4, 7, 15 Pages.

Wang et al., "IL-33 blockade suppresses tumor growth of human lung cancer through direct and indirect pathways in a preclinical model", Oncotarget, published on Aug. 2, 2017, vol. 8, No. 40, 68571-68582 Pages.

Winograd et al., "Induction of T-cell Immunity Overcomes Complete Resistance to PD-1 and CTLA-4 Blockade and Improves Survival in Pancreatic Carcinoma", Cancer Immunology Research, 2015, 14 Pages.

Dalmas et al., "Interleukin-33-Activated Islet-Resident Innate Lymphoid Cells Promote Insulin Secretion through Myeloid Cell Retinoic Acid Production", Immunity, Cell Press, Amsterdam, NL, vol. 47, No. 5, 21.

Kabacaoglu et al., "Immune Checkpoint Inhibition for Pancreatic Ductal Adenocarcinoma: Current Limitations and Future Options", Frontiers in Immunology, vol. 9, Jan. 1, 2018 (Jan. 1, 2018), p. 1878, XP055821506, DOI: 10.3389/fimmu.2018.01878.

Shen et al., "Interleukin-33 in Malignancies: Friends or Foes?", Frontiers in Immunology, vol. 9, Dec. 20, 2018 (Dec. 20, 2018), XP93047567, DOI: 10.3389/fimmu.2018.03051.

* cited by examiner

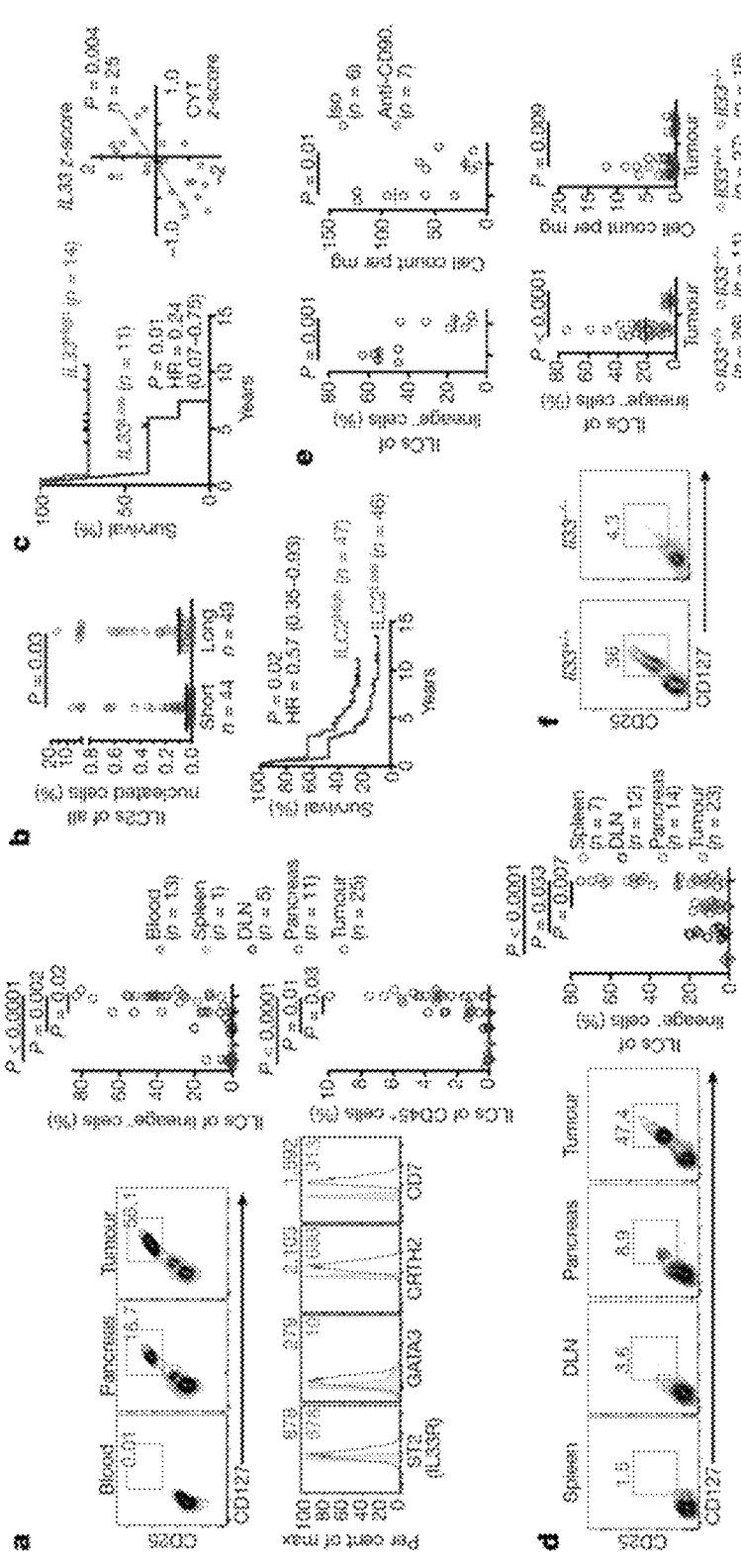
Fig. 1a-f

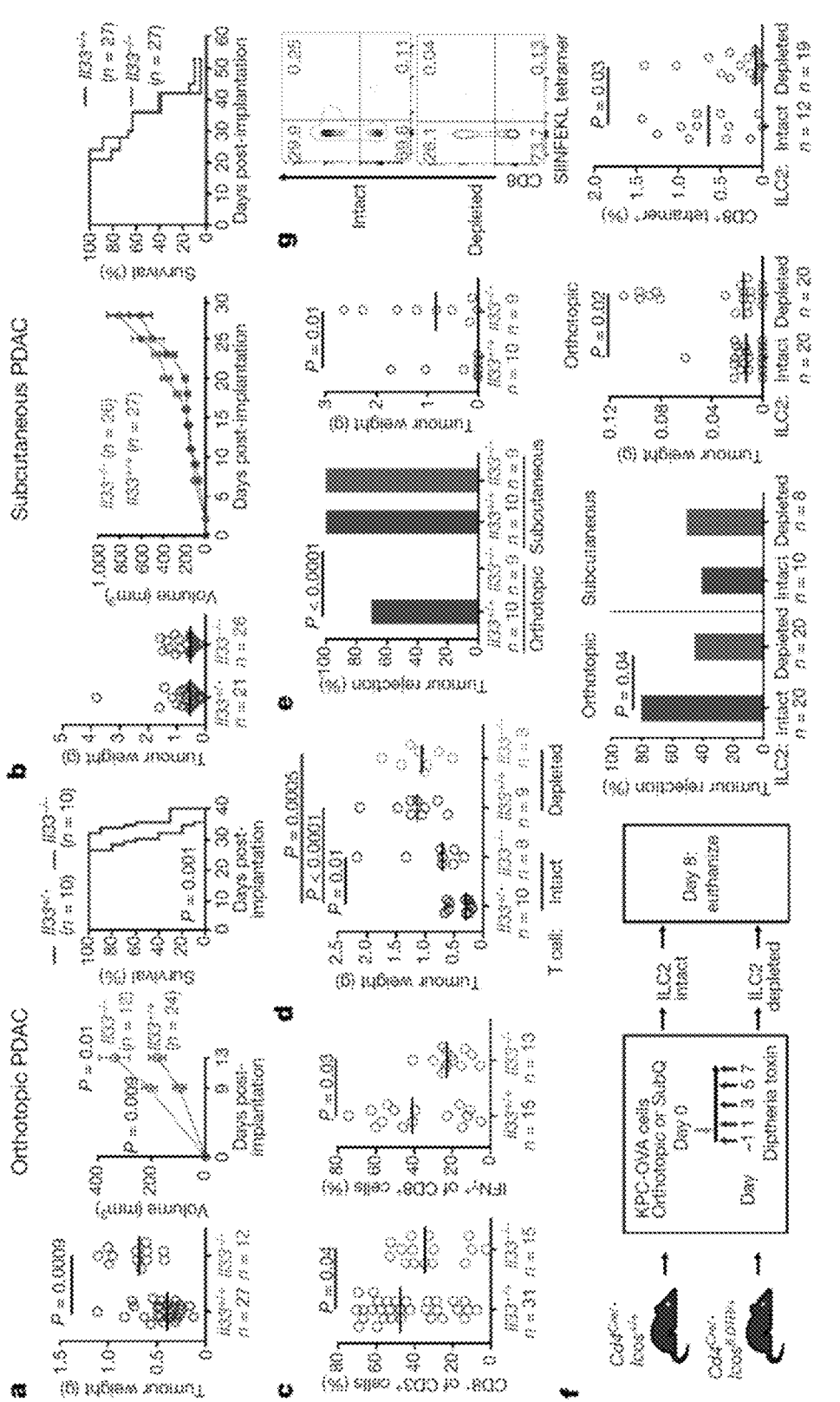
Fig. 2a-g

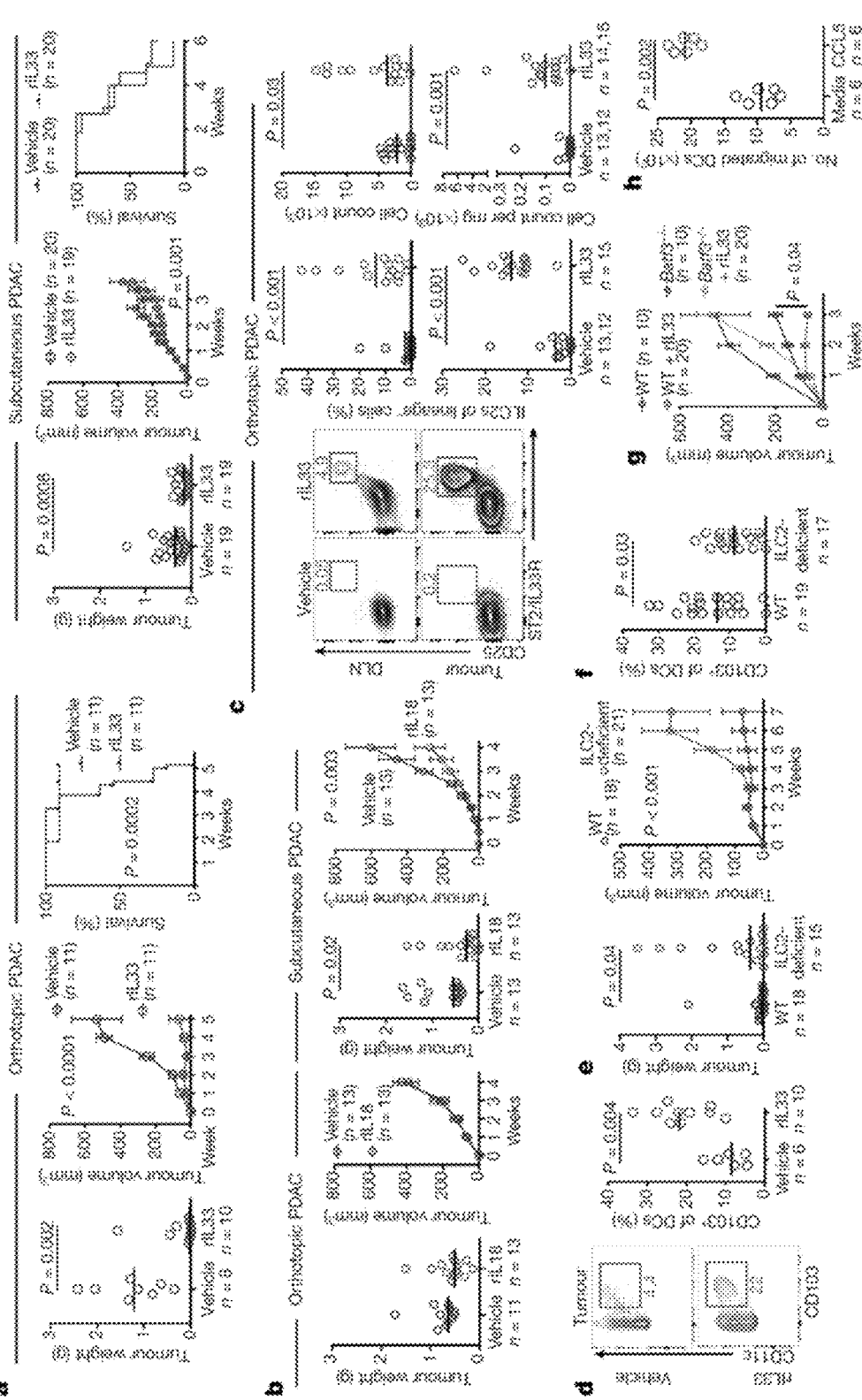
Fig. 3a-h

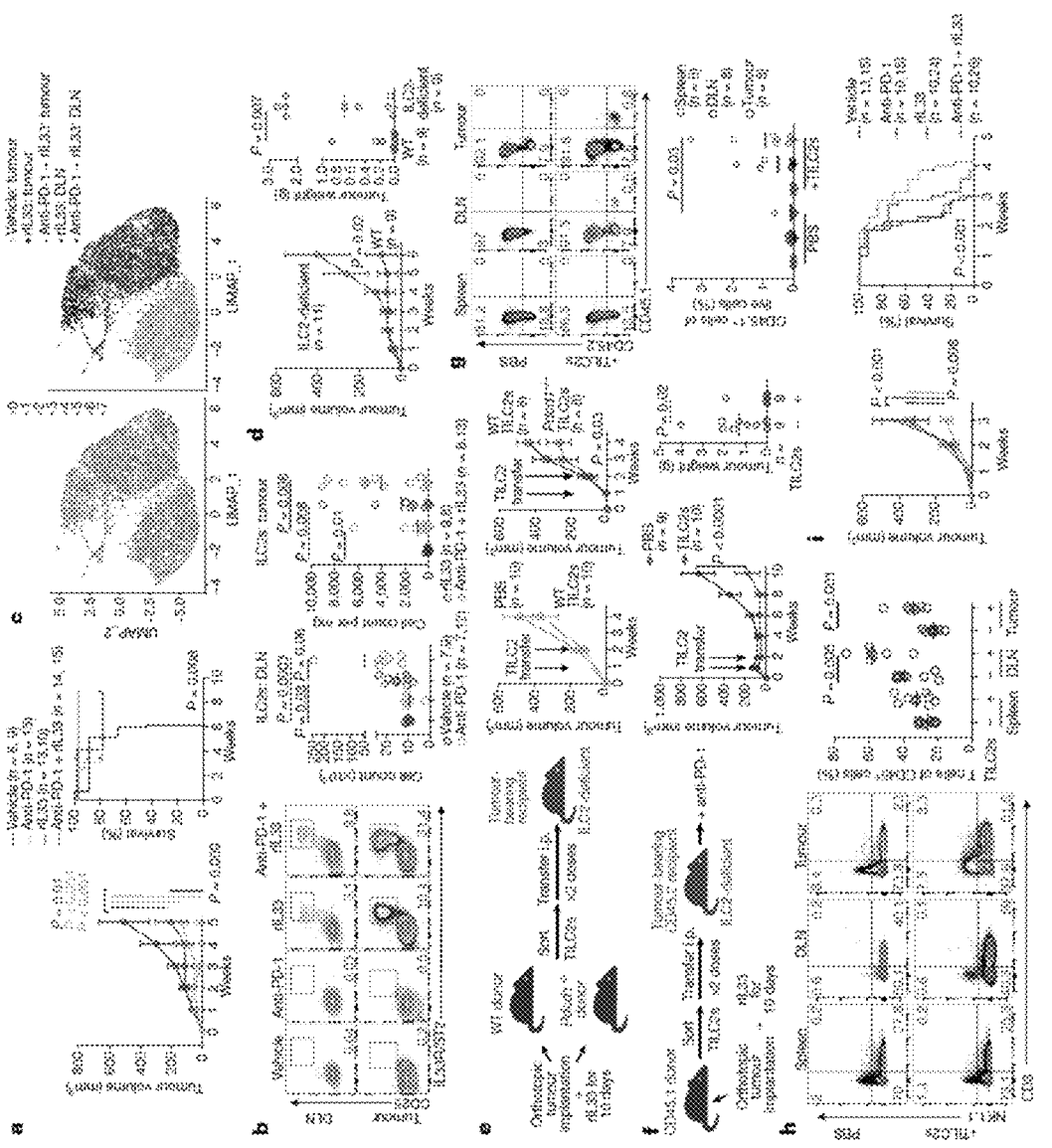
Fig. 4a-i

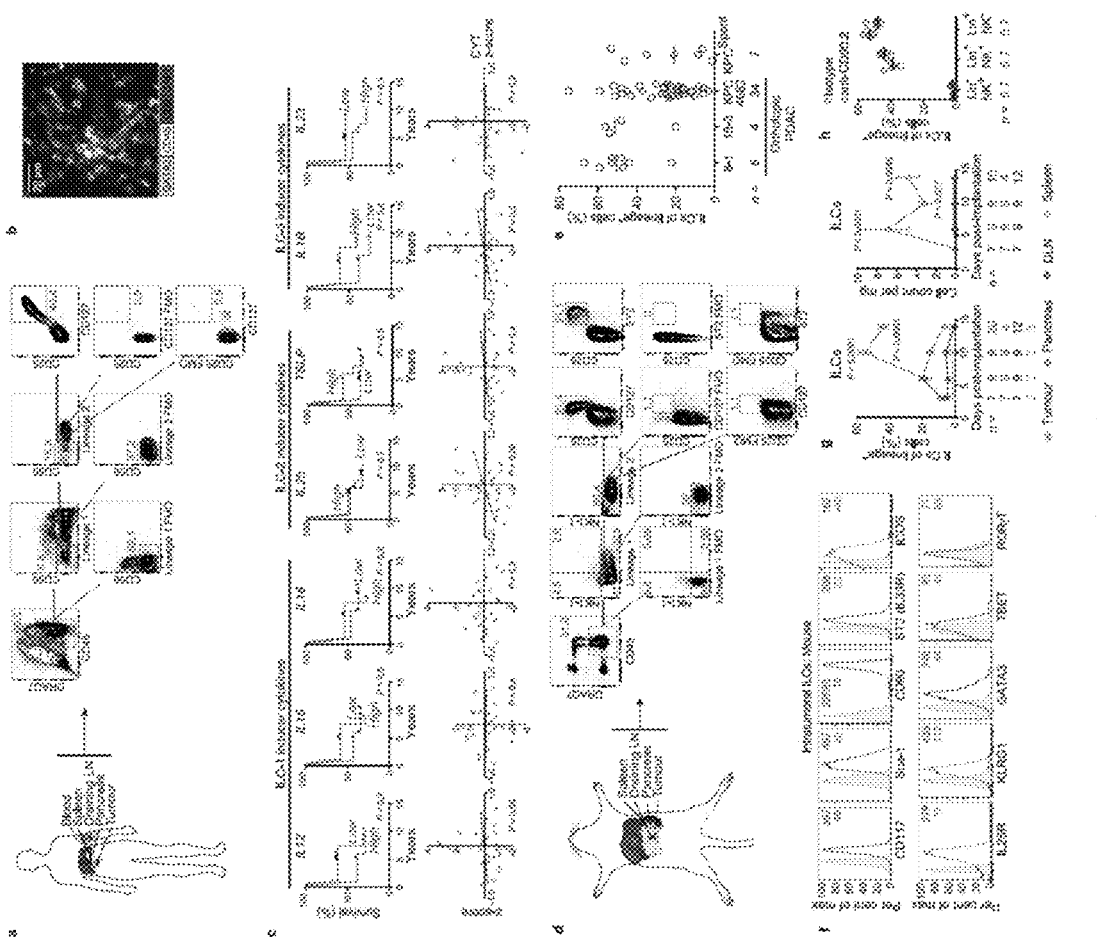
Fig. 5a-h

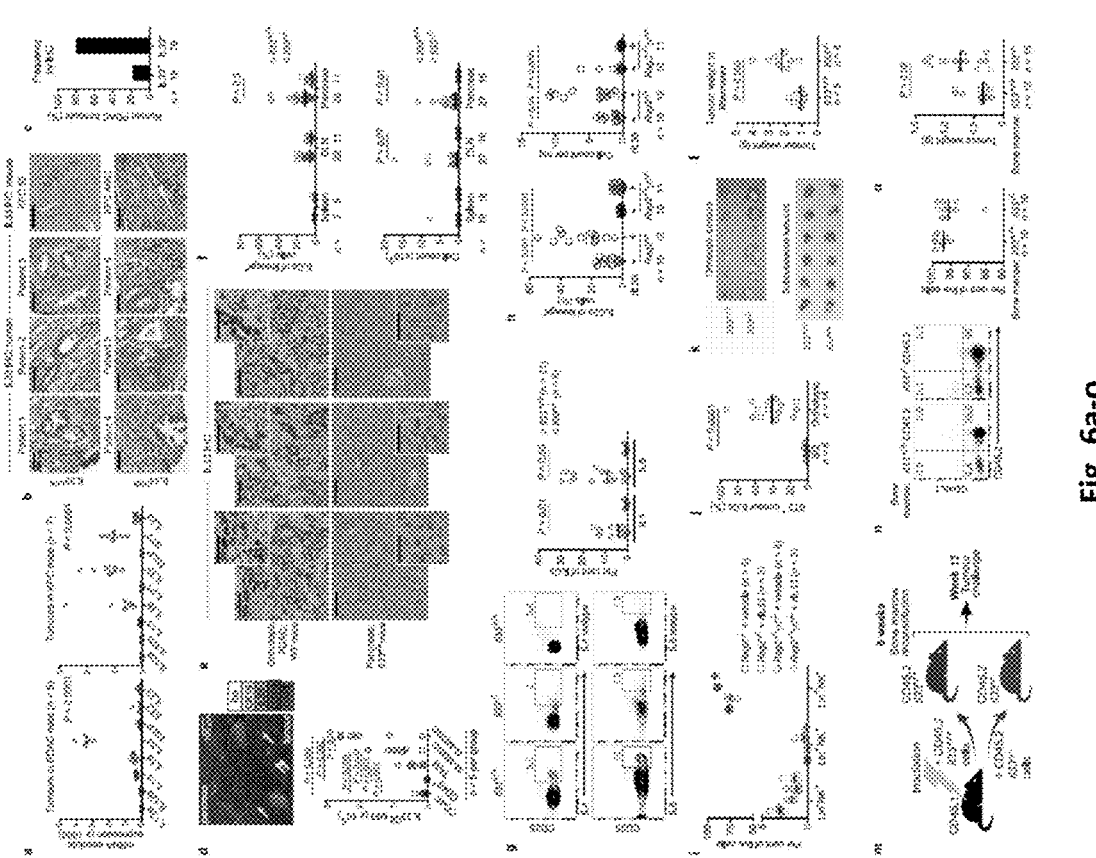
Fig. 6a-o

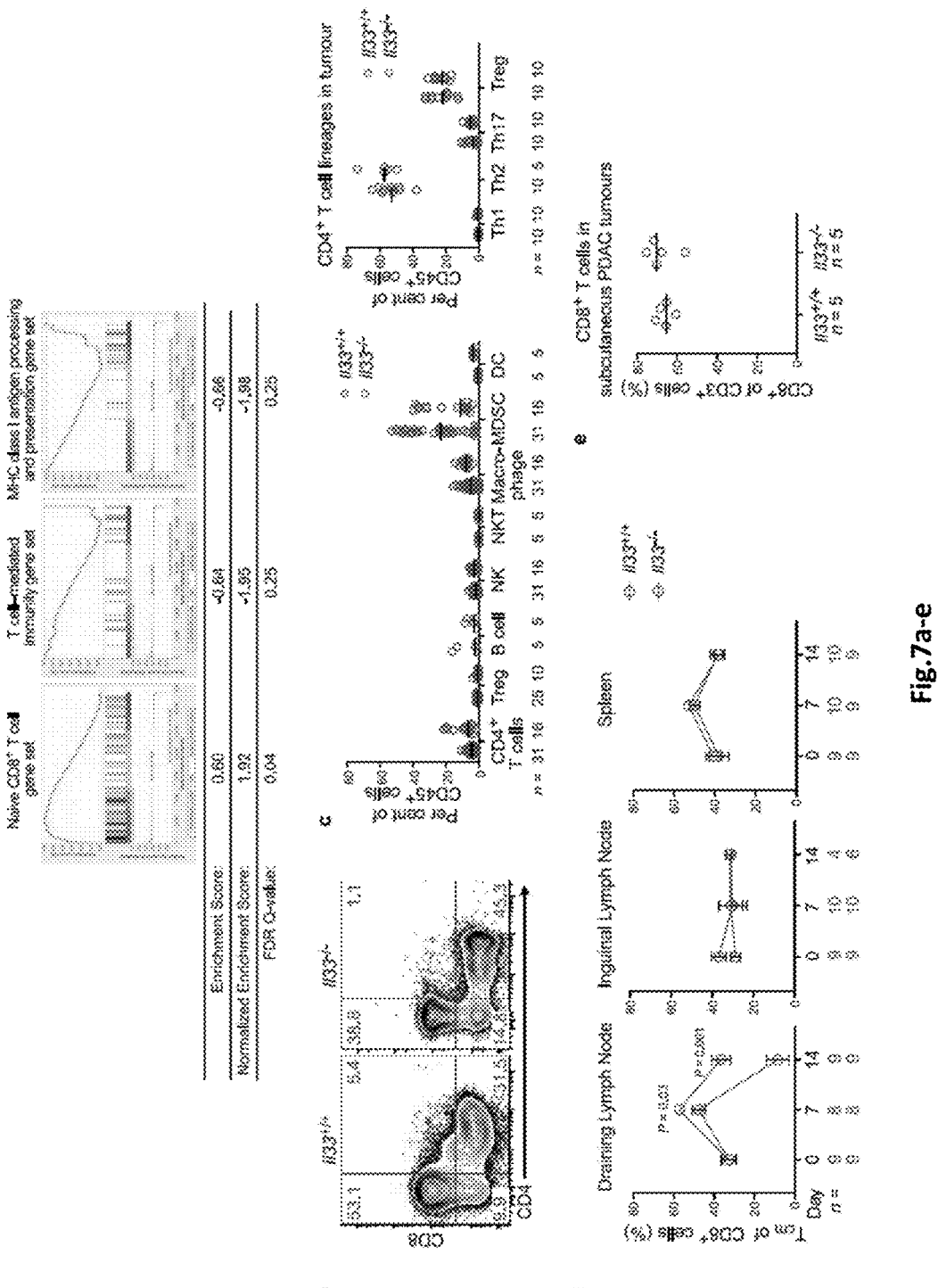
Fig.7a-e

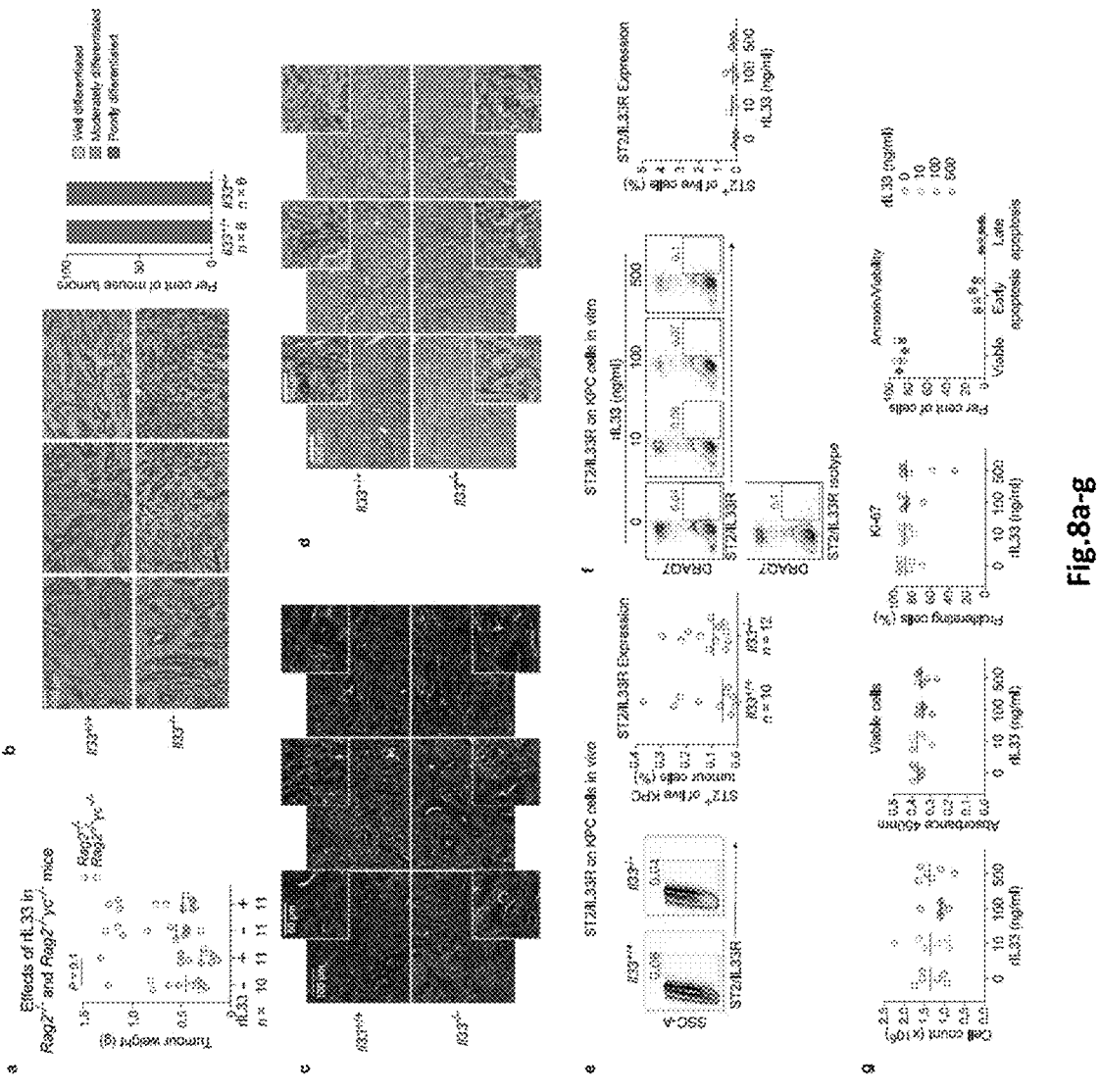
Fig. 8a-g

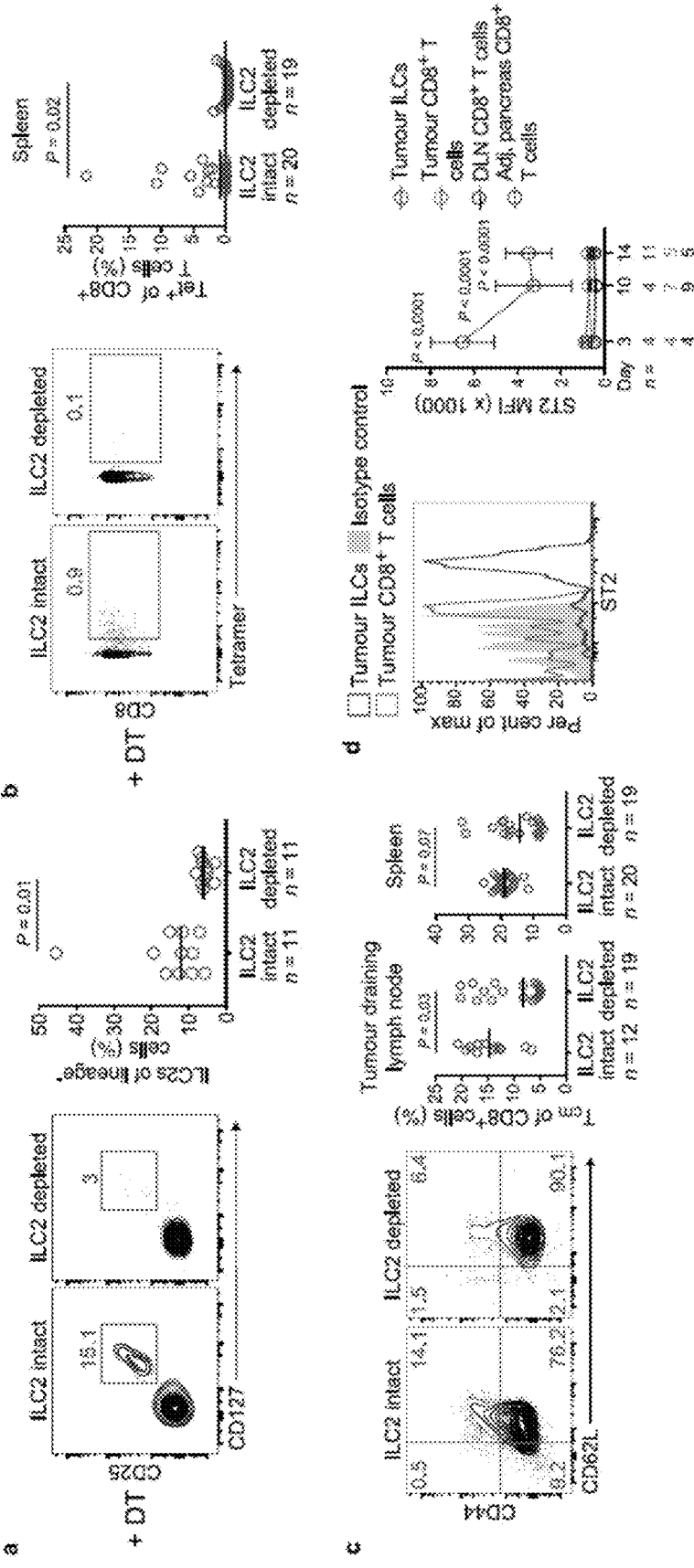
Fig. 9a-d

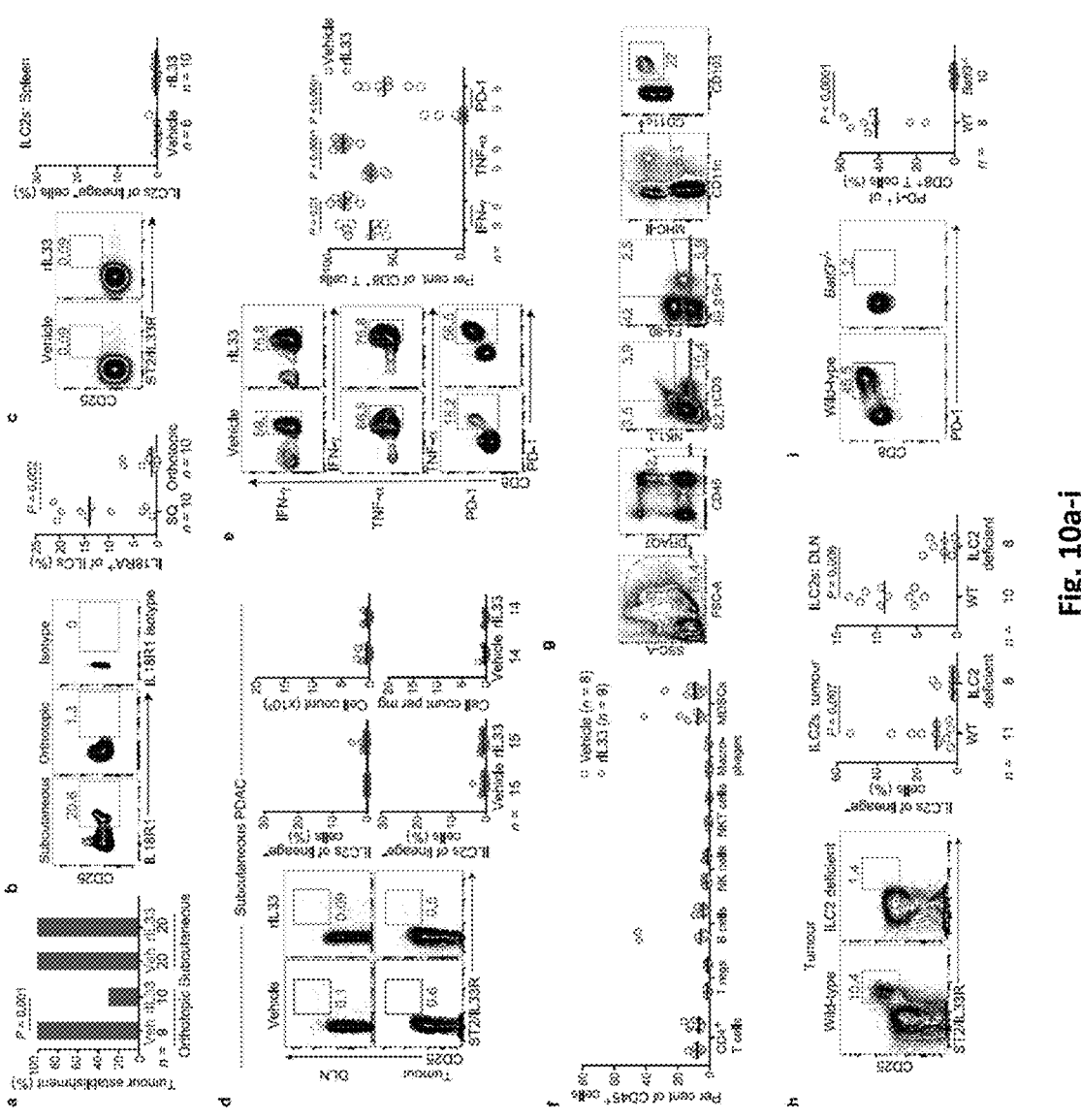
Fig. 10a-i

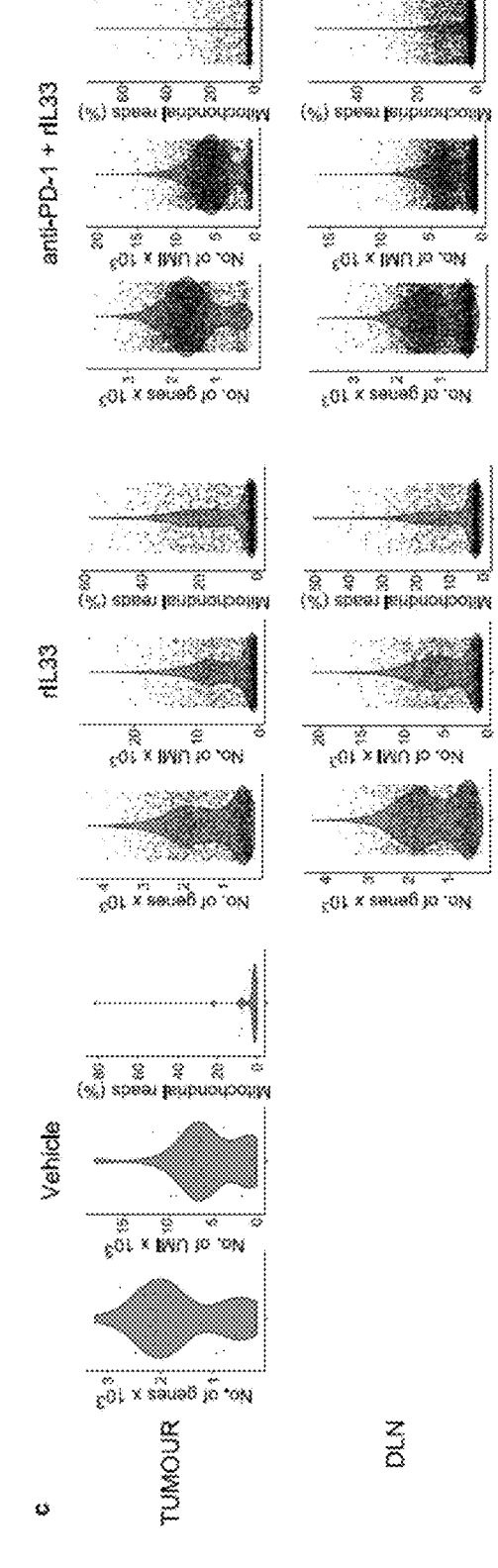
Fig. 11a-c

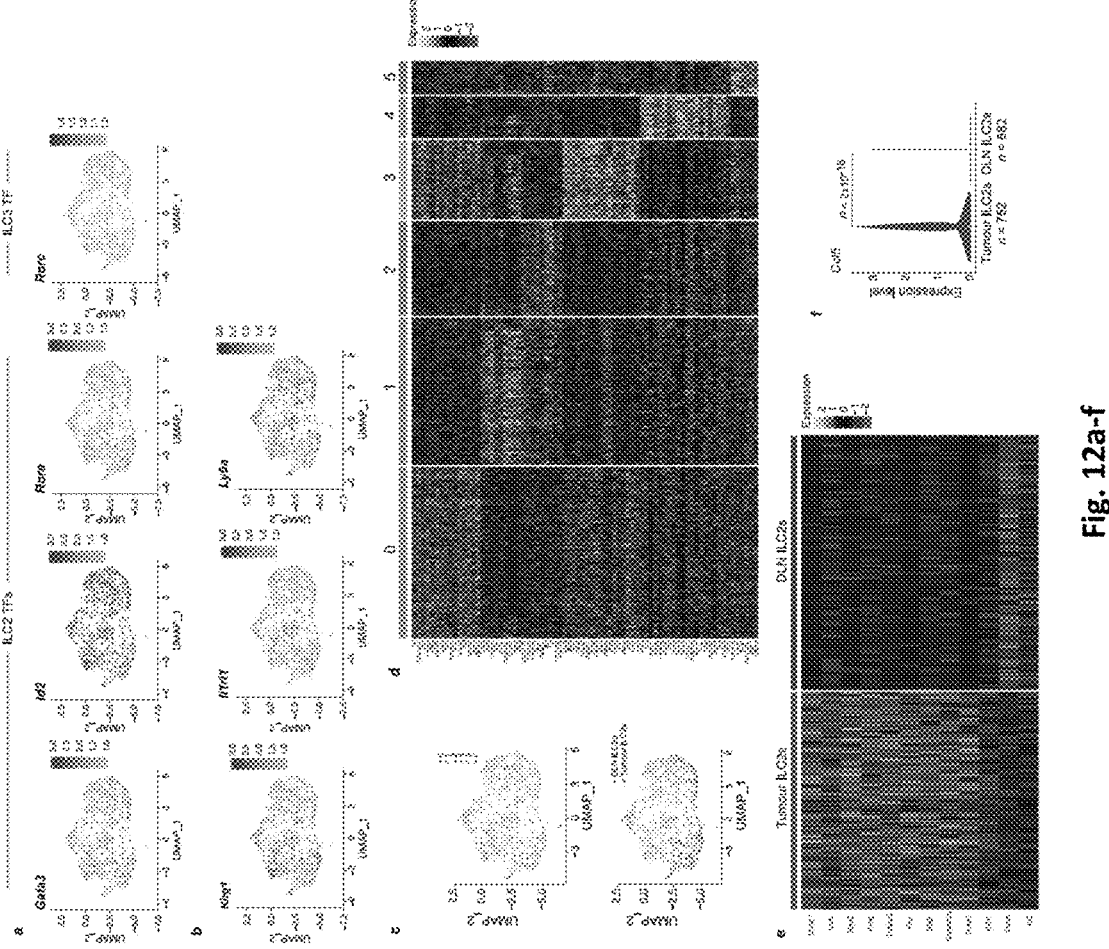
Fig. 12a-f

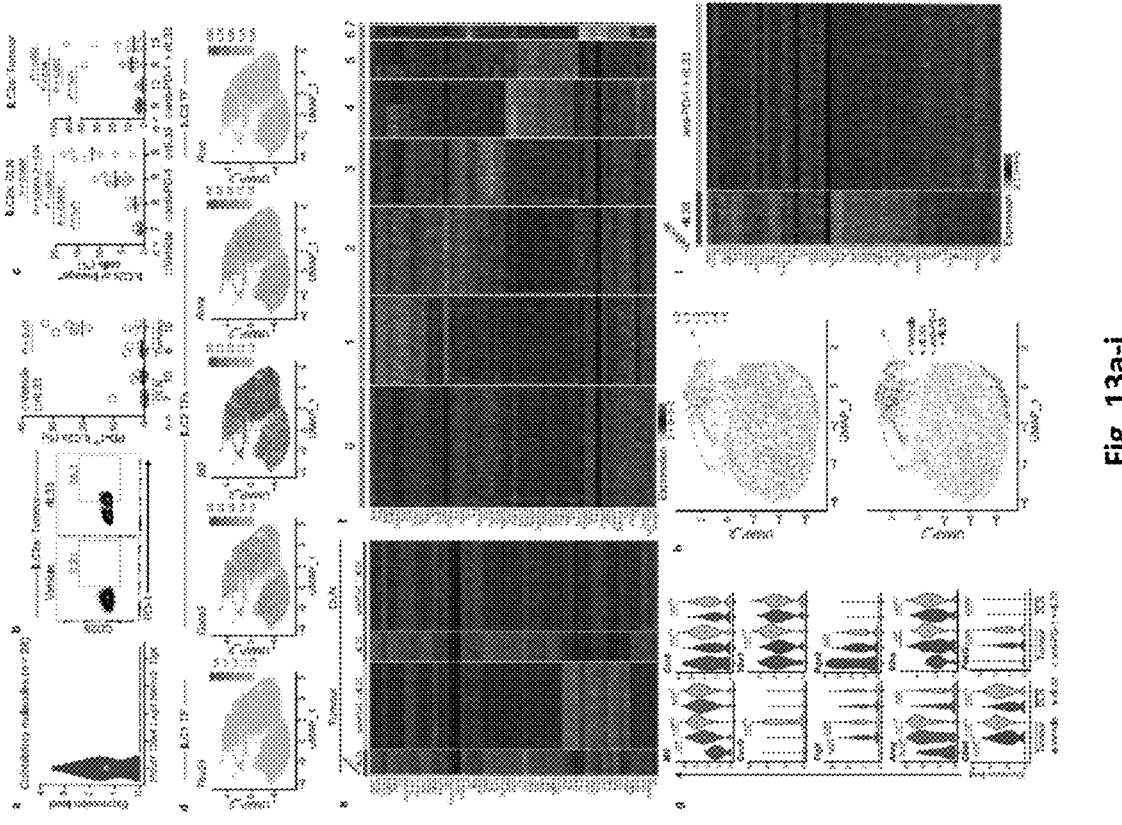
Fig. 13a-i

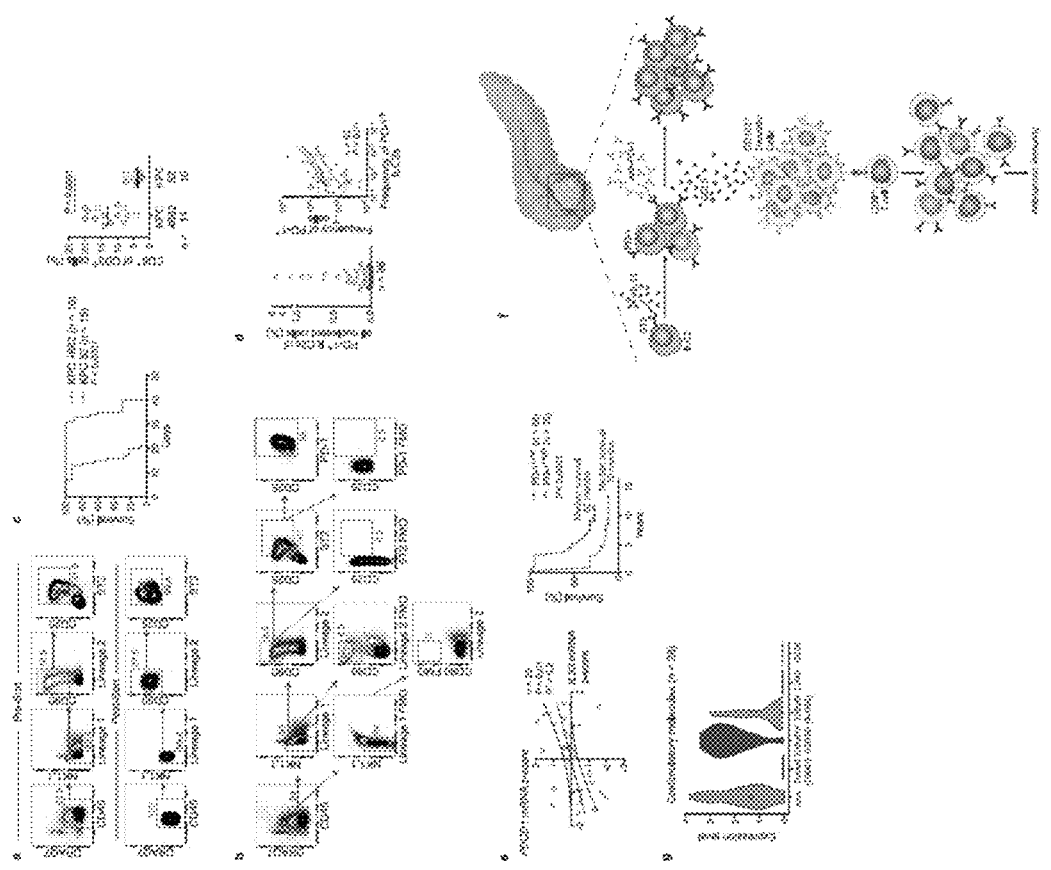
Fig. 14a-g

METHODS AND COMPOSITIONS FOR TREATMENT OF PANCREATIC CANCER

CROSS-REFERENCE TO RELATED APPLICATIONS

This application is a U.S. national stage entry under 35 USC § 371 of International Patent Application No. PCT/US202/040262 filed on Jun. 30, 2020, which claims the benefit of priority of U.S. Provisional Patent Application No. 62/868,976 filed on Jun. 30, 2019 and U.S. Provisional Patent Application No. 62/937,219 filed on Nov. 18, 2019, the content of each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jun. 30, 2020, is named MSKCC_042_WO1_SL.txt and is 15,983 bytes in size.

INCORPORATION BY REFERENCE

For the purposes of only those jurisdictions that permit incorporation by reference, all of the references cited in this disclosure are hereby incorporated by reference in their entireties. In addition, any manufacturers' instructions or catalogues for any products cited or mentioned herein are incorporated by reference. Documents incorporated by reference into this text, or any teachings therein, can be used in the practice of the present invention. Numbers in superscript following text herein refer to the numbered references identified in the "Reference List" section of this patent application.

BACKGROUND

Antibodies targeting the PD-1/PD-L1 and CTLA-4 pathways are effective cancer immunotherapies. However, most cancers lack pre-existing anti-tumor T cells and do not respond. Pancreatic ductal adenocarcinoma (PDAC) is among the most immunotherapy resistant and lethal of cancers. As such, new and improved methods of treatment of PDAC, including immunotherapy resistant PDAC, are urgently needed. The present invention addresses this need.

SUMMARY OF THE INVENTION

The present invention is based, in part, on a series of important discoveries that are described in more detail in the Examples sections of this patent specification. To briefly summarize, using a unique cohort of long-term survivors of pancreatic ductal adenocarcinoma (PDAC), it was discovered that group 2 innate lymphoid cells (ILC2s) and tumor expression of the ILC2-activating ligand interleukin (IL)-33 positively correlated with tumor immune cytolytic activity and long-term patient survival. Using PDAC mouse models, it was discovered that the IL33-ILC2 axis activates pancreatic tissue-specific anti-tumor T cell immunity. Strikingly, it was discovered that recombinant IL33 (rIL33) activated PDAC TILC2s and CD8+ T cells, curing >70% of the mice in the study. Furthermore, dual rIL33 treatment and PD-1/PD-L1 pathway blockade (using αPD-1) was found to synergistically expand pancreatic tissue-specific ILC2s and boost the anti-tumor efficacy of αPD-1 in both PD-1 partially sensitive and PD-1 resistant models. Importantly, in an extremely aggressive PD-1-resistant tumor model, while treatment with either rIL33 or αPD-1 alone had limited effect, the combination of rIL33 and αPD-1 resulted in strikingly smaller tumors than did all other treatments, with a nearly 40% reduction in tumor volume and a 50% improvement in survival. Building on these discoveries, and other discoveries presented herein, the present invention provides a variety of new and improved compositions and methods for the treatment of pancreatic cancer.

For example, in one embodiment the present invention provides a method of treating pancreatic ductal adenocarcinoma (PDAC) in a subject in need thereof, the method comprising administering to a subject with PDAC an effective amount of IL33, thereby treating the PDAC in the subject.

In another embodiment, the present invention provides a method of treating pancreatic ductal adenocarcinoma (PDAC) in a subject in need thereof, the method comprising administering to a subject with PDAC an effective amount of: (a) IL33 and (b) a PD-1 and/or PD-L1 inhibitor, thereby treating the PDAC in the subject.

In yet another embodiment, the present invention provides a method of activating pancreatic tissue-specific anti-tumor T cell immunity in a subject in need thereof, the method comprising administering to a subject with PDAC an effective amount of IL33, thereby activating tissue-specific anti-tumor T cell immunity in the subject. In some of such embodiments the activation of pancreatic tissue-specific anti-tumor T cell immunity comprises activation/expansion of pancreatic ILC2 cells and/or activation of CD8+ T cells.

In another embodiment, the present invention provides a method of activating pancreatic tissue-specific anti-tumor T cell immunity in a subject in need thereof, the method comprising administering to a subject with PDAC an effective amount of: (a) IL33 and (b) a PD-1 and/or PD-L1 inhibitor, thereby activating pancreatic tissue-specific anti-tumor T cell immunity in the subject. In some of such embodiments the activation of pancreatic tissue-specific anti-tumor T cell immunity comprises activation/expansion of pancreatic ILC2 cells and/or activation of CD8+ T cells.

In another embodiment, the present invention provides a method of activating pancreatic ILC2 cells, the method comprising contacting pancreatic ILC2 cells with an effective amount of IL33, thereby activating the pancreatic ILC2 cells.

In another embodiment, the present invention provides a method of activating pancreatic ILC2 cells, the method comprising contacting pancreatic ILC2 cells with an effective amount of: (a) IL33 and (b) a PD-1 and/or PD-L1 inhibitor, thereby activating the pancreatic ILC2 cells.

In another embodiment, the present invention provides a method of sensitizing PDAC tumors and/or pancreatic ILC2 cells to PD-1 and/or PD-L1 inhibitors, the method comprising contacting PDAC tumors and/or pancreatic ILC2 cells with an effective amount of IL33, thereby sensitizing the PDAC tumors and/or pancreatic ILC2 cells to PD-1 and/or PD-L1 inhibitors.

In some embodiments the present invention provides compositions comprising: (a) IL33 and (b) a PD-1 and/or PD-L1 inhibitor. For example, in some embodiments the present invention provides compositions for use in treatment of PDAC comprising: (a) IL33 and (b) a PD-1 and/or PD-L1 inhibitor.

In some embodiments, the methods summarized above or described elsewhere herein also include a preliminary step of determining whether the subject's tumor and/or pancreas contains ILC2 cells that express an IL-33 receptor, or a preliminary step of determining whether the ILC2 cells express an IL-33 receptor. In some of such embodiments, IL33 and/or a PD-1/PD-L1 inhibitor is only administered to the subject if the subject's tumor and/or pancreas contains ILC2 cells that express an IL-33 receptor. Similarly, in some of such embodiments, the ILC2 cells are only contacted with IL33 and/or a PD-1/PD-L1 inhibitor if the ILC2 cells express an IL-33 receptor.

In some embodiments the present invention provides various cell therapy methods. For example, in one embodiment the present invention provides a method of treating pancreatic ductal adenocarcinoma (PDAC) in a subject in need thereof, the method comprising: administering to a recipient subject with PDAC an effective amount of activated donor pancreatic ILC2 cells, wherein the donor pancreatic ILC2 cells have been obtained from a donor subject and activated ex vivo in vitro by contact with IL33, and wherein the donor subject and the recipient subject are of the same species, thereby treating the PDAC in the recipient subject.

Similarly, in another embodiment the present invention provides a method of treating pancreatic ductal adenocarcinoma (PDAC) in a subject in need thereof, the method comprising: (a) contacting donor pancreatic ILC2 cells obtained from a donor subject with IL33 ex vivo in vitro to produce activated donor pancreatic ILC2 cells, and (b) administering the donor activated pancreatic ILC2 cells to a recipient subject having pancreatic ductal adenocarcinoma (PDAC), wherein the donor subject and the recipient subject are of the same species, thereby treating the PDAC in the recipient subject.

Similarly, in yet another embodiment the present invention provides a method of treating pancreatic ductal adenocarcinoma (PDAC) in a subject in need thereof, the method comprising: (a) obtaining donor pancreatic ILC2 cells from a donor subject, (b) contacting the donor pancreatic ILC2 cells with IL33 ex vivo in vitro to produce activated donor pancreatic ILC2 cells, and (c) administering the activated donor pancreatic ILC2 cells to a recipient subject having pancreatic ductal adenocarcinoma (PDAC), wherein the donor subject and the recipient subject are of the same species, thereby treating the PDAC in the recipient subject.

In some embodiments the cell therapy methods described above or elsewhere herein also comprise a step of expanding the donor pancreatic ILC2 cells and/or activated donor pancreatic ILC2 cells ex vivo in vitro prior to administering the activated donor pancreatic ILC2 cells to the recipient subject. In some of the cell therapy methods described above or elsewhere herein the donor pancreatic ILC2 cells administered to recipient subjects are a substantially pure population of ILC2 cells. Such substantially pure populations of ILC2 cells can be obtained by any suitable cell isolation/ purification methods, such as by cell sorting based on the presence of one or more pancreatic ILC2 markers (such as those described in the Examples section of this patent specification). In some of the cell therapy methods described above or elsewhere herein the donor subject and the recipient subject are the same individual, such that the method is an autologous cell therapy method. Similarly, in some of the cell therapy methods described above or elsewhere herein the donor subject and the recipient subject have same MHC/HLA type.

In some of the embodiments summarized above or described elsewhere herein, the subject (including the donor and/or recipient subject in the case of cell therapy methods)

is a human. In some of the embodiments summarized above or described elsewhere herein, the subject (including the donor and/or recipient subject in the case of cell therapy methods) is a non-human mammal. In some of the embodiments summarized above or described elsewhere herein, the subject (including the donor and/or recipient subject in the case of cell therapy methods) is a mouse. In some of the embodiments summarized above or described elsewhere herein, the subject (including the donor and/or recipient subject in the case of cell therapy methods) has a PDAC that is partially or totally resistant to PD-1 and/or PD-L1 inhibitor treatment.

In some of the embodiments summarized above or described elsewhere herein, the IL33 is recombinant IL33. In some of the embodiments summarized above or described elsewhere herein, the IL33 is human IL33. In some of the embodiments summarized above or described elsewhere herein, the IL33 is recombinant human IL33. In some of the embodiments summarized above or described elsewhere herein, the IL33 is mouse IL33. In some of the embodiments summarized above or described elsewhere herein, the IL33 is recombinant mouse IL33.

In those embodiments summarized above or described elsewhere herein that involve a PD-1 inhibitor, in some of such embodiments the PD-1 inhibitor is an antibody. In some of the embodiments summarized above or described elsewhere herein, the PD-1 inhibitor is selected from the group consisting of pembrolizumab, nivolumab, cemiplimab, AMP-224, AMP-514 and PDR001.

In those embodiments some of the embodiments summarized above or described elsewhere herein that involve a PD-L1 inhibitor, in some of such embodiments the PD-L1 inhibitor an antibody. In some embodiments the PD-L1 inhibitor is selected from the group consisting of atezolizumab, avelumab, durvalumab, BMS-936559 and CK-301.

These and other aspects of the present invention are described further in the Detailed Description, Drawings, and Examples sections of this patent application. Furthermore, one of skill in the art will recognize that the various embodiments of the present invention described throughout this patent disclosure can be combined in various different ways, and that such combinations are within the scope of the present invention.

BRIEF DESCRIPTION OF THE DRAWINGS

FIG. 1a-f: IL33-dependent ILC2s infiltrate human and murine pancreatic cancer. (FIG. 1a) Gating, frequency, and phenotype of ILCs in unselected human PDAC patients. (FIG. 1b) Frequency (top) and survival association (bottom) of ILC2s in tumor tissue microarrays of short-term and long-term PDAC survivors. (FIG. 1c) Bulk tumor IL33 mRNA associations with survival and correlation with tumor cytolytic index (CYT) in short- and long-term PDAC survivors. (FIG. 1d) Gating and frequency of ILCs in PDAC mice. (FIG. 1e) Intratumoral ILC frequency and number in Rag2$^{-/-}$ PDAC mice treated with αCD90.2 or isotype (Iso) antibodies. (FIG. 1f) Gating, frequency, and number of ILCs in Il33$^{+/+}$ and Il33$^{-/-}$ PDAC mice. High and low in FIG. 1b, FIG. 1c defined as higher or lower, respectively, than the median for the cohort. Data were collected at 14 (FIG. 1d-f) post tumor implantation. n, number of tumors from individual patients or mice. Horizontal bars mark medians. Data in FIG. 1d-f are pooled from ≥2 independent experiments with n≥3/group; each point indicates one mouse analyzed separately. P values determined by one-way ANOVA with Tukey's (FIG. 1a) and Kruskal-Wallis multiple comparison post-tests (FIG. 1*d*), two-tailed Mann-Whitney test (b, e, f), two-sided log-rank FIG. 1 (b, c survival curves), and linear regression (FIG. 1*c*).

FIG. 2*a-g*: The IL33-ILC2 axis activates tissue-specific cancer immunity. Tumor weight, volumes, and survival of Il33$^{+/+}$ and Il33$^{-/-}$ orthotopic (FIG. 2*a*) or subcutaneous (FIG. 2*b*) PDAC mice. (FIG. 2*c*) Frequency of all (left) and IFN-γ producing (right) CD8$^+$ T cells in orthotopic Il33$^{+/+}$ and Il33$^{-/-}$ PDAC tumors. (FIG. 2*d*) Tumor weight in T cell-depleted Il33$^{+/+}$ and Il33$^{-/-}$ orthotopic PDAC mice. (FIG. 2*e*) Frequency of tumor rejection and tumor weight in Il33$^{+/+}$ and Il33$^{-/-}$ orthotopic and subcutaneous KPC-OVA PDAC mice. (FIG. 2*f*) Experimental design (left), frequency of tumor rejection (middle), and tumor weight (right) of KPC-OVA PDAC tumors in iCOS-T mice with intact or depleted ILC2s. (FIG. 2*g*) Frequency of OVA-specific CD8$^+$ T cells in draining lymph nodes of orthotopic KPC-OVA PDAC iCOS-T mice with intact or depleted ILC2s. Data were collected at 14 days (FIG. 2*a, c, d*), 28 days (FIG. 2*b*), 42 days (FIG. 2*e*), and 8 (FIG. 2*f, g*) days post implantation. Horizontal bars mark medians, error bars mark s.e.m. Data were pooled from ≥2 independent experiments with n≥4/group; n and data points denote individual mice analyzed separately. P values were determined by two-tailed Mann-Whitney test (FIG. 2*a-g*), two-sided log-rank test (FIG. 2*a, b*, survival curves), two-way ANOVA with Sidak's multiple comparison test (FIG. 2*a, b*, tumor volumes), and Chi-square test (FIG. 2*e, f* % rejection).

FIG. 3*a-h*: ILC2s stimulate tissue-specific cancer immunity by recruiting intratumoral dendritic cells. (FIG. 3*a*) Tumor weight, volume, and survival in orthotopic and subcutaneous PDAC mice treated with vehicle or recombinant IL33 (rIL33). (FIG. 3*b*) Tumor weight and volume in orthotopic and subcutaneous PDAC mice treated with vehicle or recombinant IL18 (rIL18). (FIG. 3*c*) Gating, frequency, and number of ILC2s in rIL33-treated orthotopic PDAC mice (DLN vehicle, n=13; tumor vehicle, n=12). (FIG. 3*d*) Gating and frequency of CD103$^+$ dendritic cells (DCs) in tumors of rIL33-treated orthotopic PDAC mice. (FIG. 3*e*) Tumor weight, volume, and (FIG. 3*f*) frequency of CD103$^+$ DCs in tumors of rIL33-treated wild-type (WT) and ILC2 deficient orthotopic PDAC mice. (FIG. 3*g*) Tumor volume in rIL33-treated WT and CD103$^+$ DC deficient Batf3$^{-/-}$ orthotopic PDAC mice. (FIG. 3*h*) Migration of purified DCs towards Ccl5. Data were collected at 5 (FIGS. 3*c, d*) and 7 (FIG. 3*e, f*) weeks post tumor implantation. Horizontal bars mark medians; error bars mark s.e.m. Data were pooled from ≥2 independent experiments, with n≥3/group; n and data points denote individual mice analyzed separately or (FIG. 3*h*) individual replicates. P values were determined by two-sided log-rank test (FIG. 3*a*, survival curve), two-way ANOVA (FIG. 3*a, b, e, g*, tumor volume), and two-tailed Mann-Whitney test (FIG. 3*a-f, h*).

FIG. 4*a-i*: PD-1 blockade activates TILC2s. (FIG. 4*a*) Tumor volume and survival, (FIG. 4*b*) gating, frequency and number and (FIG. 4*c*) scRNA-seq (n=7,022 ILC2 single cells) in treated PDAC mice in a nonlinear representation of the top 15 principal components. Cells are colored by cluster (left) or treatment and tissue (right). In (FIG. 4*a, b*) n=n in left, right graphs respectively. (FIG. 4*d*) Tumor volume in wild-type (WT) or ILC2 deficient PDAC mice treated with αPD-1+rIL33. (FIG. 4*e*) TILC2s were sort-purified from rIL33-treated WT or Pdcd1$^{-/-}$ PDAC mice, transferred into ILC2-deficient PDAC recipients, and tumor volumes measured. (FIG. 4*f-h*) TILC2s were sort-purified from rIL33-treated PDAC CD45.1 donor mice, transferred into ILC2-deficient CD45.2 PDAC recipient mice, and treated with αPD-1 post cell transfer. Tumor volume and tumor weight (FIG. 4*f*), frequency of CD45.1 and CD45.2 cells (FIG. 4*g*), and frequency of T cells (FIG. 4) (TILC2s-: all groups, n=8; TILC2+: spleen, n=9; DLN, n=7; tumor, n=7) in recipient mice 10 weeks post cell transfer. Frequencies in FIG. 4*g*=percentage of live donor- or recipient-derived immune cells. (FIG. 4*i*) Tumor volume (vehicle, n=13; other groups, n=10) and survival (vehicle and αPD-1, n=15; rIL33, n=24; rIL33+αPD-1, n=26) of treated PDAC mice (KPC 52 cells). DLN, draining lymph node. Data were collected at 5 weeks (FIG. 4*b*), 10 days (FIG. 4*c*), and 6 weeks (FIG. 4*d*) post orthotopic tumor cell implantation. Horizontal bars mark medians, error bars mark s.e.m. Data are pooled from ≥2 independent experiments with n≥3/group; n and data points denote individual mice analyzed separately. Data for scRNA-seq represent pooled purified single cells from biological replicates (vehicle n=10, rIL33 n=5, αPD-1+rIL33 n=5). P values were determined by two-way ANOVA with Tukey's multiple comparison post (FIG. 4*a, d-f, i*, tumor volume), two-tailed Mann-Whitney (FIG. 4*b, d, g, h*), and two-sided log-rank (FIG. 4*a, i*, survival curves) tests.

FIG. 5*a-h*: Identification of IL33-dependent ILCs in pancreatic cancer. (FIG. 5*a*) Gating strategy to identify human ILCs. The first plot was pre-gated on live (DRAQ7$^-$) cells and singlets. Lineage (Lin) 1 cocktail: CD5, CD11b, CD11c, CD16, FcεR1. Lin 2 cocktail: CD3, CD19, TCRα/β. ILCs were identified as Lin$^-$ CD56$^-$ CD25$^+$ CD127$^+$ cells. FMO, fluorescence minus one. (FIG. 5*b*) Representative image of immunofluorescence of ILC2s in tumor tissue microarrays of short-term and long-term PDAC survivors (n=96). Arrows, putative ILC2s. (FIG. 5*c*) Top, overall survival of patients with greater (high) or lesser (low) than the median intratumoral mRNA level of ILC-stimulating cytokines. Bottom, correlation between expression of ILC-activating cytokines and immune cytolytic index (CYT) in long- and short-term survivors of human PDAC. Curves were fit by linear regression. n=25. (FIG. 5*d*) Gating strategy to identify murine ILCs. The first plot was pre-gated on live (DRAQ7$^-$) cells and singlets. Lineage (Lin) 1 cocktail: CD5, CD11b, CD11c, FcεR1. Lin 2 cocktail: CD3, CD19. ILCs were identified as Lin$^-$ NK1.1$^-$ CD25$^+$ CD127$^+$, ILC2s as Lin$^-$ NK1.1$^-$ CD25$^+$ St2$^+$ cells. Gating on orthotopic PDAC mice are shown. (FIG. 5*e*) Intratumoral ILC frequency in orthotopic PDAC mice established with KPC cell lines 8-1, 18-3, and in autochthonous KPC mice with spontaneous PDAC (KPC$^{Spont}$). Composite ILC frequencies from FIG. 1*d* and others are included for comparison (KPC 4662). (FIG. 5*f*) Phenotype of ILCs in PDAC mice. Gray curves, isotype controls; numbers, mean fluorescence intensity. (FIG. 5*g*) Expansion kinetics of ILCs in tissues of PDAC mice. (FIG. 5*h*) Changes in non-ILC cell frequency in Rag2$^{-/-}$ PDAC mice treated with αCD90.2 or isotype antibodies. Data were analyzed at 14 days (FIG. 5*d-f*), 10 days (FIG. 5*h*), or at the indicated time points post tumor implantation. n indicates individual mice analyzed separately in at least two independent experiments with n≥2/group. Horizontal bars mark medians, error bars mark s.e.m. P values were determined by two-sided log-rank (FIG. 5*c*, top), linear regression (FIG. 5*c*, bottom), or two-tailed Mann-Whitney test (FIG. 5*g*). P values in FIG. 5*g* indicate tumor comparisons to all other organs.

FIG. 6*a-o*: Host-derived IL33 activates pancreatic ILC2s. (FIG. 6*a*) mRNA expression of ILC1- (IL12, IL15, IL18), ILC2-(IL25, IL33, TSLP), and ILC3-inducer cytokines (IL23) and the IL33 receptor (ST2) in orthotopic PDAC tumors (left) and autochthonous PDAC tumors in KPC mice from a previously published mRNA microarray (right)[11].

(FIG. 6*b*) Representative IL33 immunohistochemistry (IHC) of IL33$^{Low}$ and IL33$^{High}$ human (tissue microarray, n=96) and mouse PDAC (n=3/group). (FIG. 6*c*) Frequency of human PDAC patients demonstrating IL33 positivity by IHC in a human PDAC tumor microarray. (FIG. 6*d*) Multiplexed immunofluorescence for IL33, ductal marker CK19, and myeloid markers CD11b, and Iba in mouse PDAC (top). Arrows, IL33-expressing cells. IL33 mean fluorescence intensity (MFI) in non-immune (CD45$^-$), immune (CD45$^+$), macrophage (TAM), and monocytic and granulocytic myeloid-derived suppressor cell (M-MDSC and G-MDSC) populations in tumors of IL33$^{Cit}$ reporter PDAC mice (bottom). (FIG. 6*e*) Representative IL33 protein expression by IHC in orthotopic PDAC tumors in Il33$^{+/+}$ (WT) mice, and non-tumor-bearing pancreata in Il33$^{-/-}$ mice (n=3/group). (FIG. 6*f*) ILC frequency (top) and cell number (bottom) in organs and draining lymph nodes (DLN) of Il33$^{+/+}$ and Il33$^{-/-}$ orthotopic PDAC mice. (FIG. 6*g*) Gating and frequency of IL4 and IL5 expression in intratumoral ILCs in Il33$^{+/+}$ and Il33$^{-/-}$ orthotopic PDAC mice. (FIG. 6*h*) ILC2 and (FIG. 6*i*) immune cell frequencies in orthotopic Rag2$^{-/-}$ and Rag2$^{-/-}$ γ$_c^{-/-}$ PDAC mice with or without treatment with recombinant IL33 (rIL33). (FIG. 6*j*) Frequency of ST2 tumor ILCs in mice with subcutaneous (SQ) and orthotopic PDAC. (k) Tumors in orthotopic and subcutaneous PDAC mice. (FIG. 6*l*) Tumor weight in Il33$^{+/+}$ and Il33$^{-/-}$ littermate PDAC mice. (FIG. 6*m*) Experimental schema of bone-marrow chimeras to evaluate contribution of hematopoietic cell-derived IL33 to tumor control. (FIG. 6*n*) Hematopoietic cell reconstitution and (FIG. 6*o*) tumor weight in irradiated CD45.1 congenic mice reconstituted with either CD45.2 Il33$^{+/+}$ or CD45.2 Il33$^{-/-}$ bone marrow. Data were collected at 14 (FIGS. 6*a, d, f, g, j, o*), and 10 (FIG. 6*h, i*) days post tumor implantation. Horizontal bars mark medians. n indicates individual mice analyzed separately in at least two independent experiments with n≥2/group. P values were determined by one-way ANOVA (FIG. 6*a*) or two-tailed Mann-Whitney test (FIG. 6*d, f-h, j, l, o*).

FIG. 7*a-e*: Host-derived IL33 activates pancreatic T cell immunity. (FIG. 7*a*) Gene set enrichment analysis of bulk RNA-seq from purified CD45+ immune cells from Il33$^{+/+}$ and Il33$^{-/-}$ PDAC mice. Enrichment plots and enrichment scores are shown for three gene sets comparing expression in Il33$^{-/-}$ to Il33$^{+/+}$ (n=3 mice/group). FDR, false discovery rate. (FIG. 7*b*) Gating of CD8$^+$ T cells and (FIG. 7*c*) frequencies of various immune cell types (left) and CD4$^+$ T cell lineages (right) in Il33$^{+/+}$ and Il33$^{-/-}$ orthotopic PDAC mice. (FIG. 7*d*) Frequency of T central memory (T$_{cm}$) cells (CD45$^+$CD3$^+$CD8$^+$CD44$^+$CD62L$^+$) in tumor draining lymph nodes and non-tumor draining distant lymphoid organs (inguinal lymph node and spleen) in Il33$^{+/+}$ and Il33$^{-/-}$ orthotopic PDAC mice. (FIG. 7*e*) Frequency of CD8$^+$ T cells in subcutaneous PDAC tumors. DC, dendritic cells; MDSC, myeloid-derived suppressor cells; NK, natural killer cells; NKT, natural killer T cells; T$_{reg}$, regulatory T cells. Data were analyzed 14 days post tumor implantation or at the time points indicated. Horizontal bars mark medians, error bars mark s.e.m. n indicates individual mice analyzed separately in at least two independent experiments with n≥2/group. P values determined by one-way ANOVA (FIG. 7*d*).

FIG. 8*a-g*: IL33 and ILCs do not directly induce tumor cell death. (FIG. 8*a*) Tumor weight in Rag2$^{-/-}$ and Rag2$^{-/-}$ γc$^{-/-}$ PDAC mice treated with vehicle or recombinant murine IL33 (rIL33). (FIG. 8*b*) Representative hematoxylin and eosin stained sections (left) with histologic tumor cell differentiation status in Il33$^{+/+}$ and Il33$^{-/-}$ PDAC mice (right). (FIG. 8*c*) Trichrome staining in tumors of Il33$^{+/+}$ and Il33$^{-/-}$ PDAC mice (n=3/group). (FIG. 8*d*) Immunohistochemistry for smooth muscle actin in tumors of Il33$^{+/+}$ and Il33$^{-/-}$ PDAC mice (n=3/group). (FIG. 8*e*) Intratumoral ST2 expression on KPC cells in Il33$^{+/+}$ and Il33$^{-/-}$ orthotopic PDAC mice. (FIG. 8*f*) ST2 expression on live KPC cells following rIL33 treatment in vitro (DRAQ7 stains dead cells) (n=3/group). (FIG. 8*g*) KPC cell number, viability, proliferation (Ki-67), and apoptosis (annexin) following rIL33 treatment in vitro (n=6/group). Horizontal bars mark medians. n in FIG. 8*a-e* indicates individual mice analyzed separately in at least two independent experiments with n≥3/group. n in FIG. 8*f, g* indicates technical replicates and is representative of at least two independent experiments. P value determined by two-tailed Mann-Whitney test (FIG. 8*a*).

FIG. 9*a-d*: ILC2s induce antigen-specific CD8+ T cell priming. (FIG. 9*a*) Gating and frequency of intratumoral ILC2s in ILC2-intact mice (diphtheria toxin [DT]-treated Icos$^{+/+}$; CD4$^{Cre/+}$) and ILC2-depleted mice (DT-treated Icosfl.$^{DTR/+}$; CD4$^{Cre/+}$). (FIG. 9*b*) Gating and frequency of OVA-specific CD8$^+$ T cells in spleens from ILC-intact and ILC-depleted mice. OVA-specific T cells were detected as SIINFEKL (SEQ ID NO. 15)-tetramer$^+$ cells. (FIG. 9*c*) Gating and frequency of central memory CD8$^+$ T (T$_{CM}$) cells (CD45$^+$CD3$^+$CD8$^+$CD44$^+$CD62L$^+$) in tumor draining lymph nodes and spleens in ILC-intact and ILC-depleted mice. (FIG. 9*d*) ST2 expression on CD45$^+$CD3$^+$CD8$^+$ T cells after tumor implantation in PDAC mice. Data were collected at 14 days post tumor implantation or at the time points indicated. DLN, draining lymph node; MFI, mean fluorescence intensity. Horizontal bars mark medians; error bars mark s.e.m. n indicates individual mice analyzed separately in at least two independent experiments with n≥2/group. P values determined by two-tailed Mann-Whitney test (FIG. 9*a-c*) and two-way ANOVA with Tukey's multiple comparison post-test (FIG. 9*d*, indicating comparison of tumor ILCs to all other groups).

FIG. 10*a-i*: Immunophenotyping in rIL33-treated PDAC mice. (FIG. 10*a*) Percent tumor establishment of orthotopic and subcutaneous KPC-OVA PDAC tumors in vehicle (veh) and rIL33 treated mice. (FIG. 10*b*) Gating (left) and frequency (right) of IL18R1 expression on tumor ILCs in subcutaneous (SQ) and orthotopic PDAC mice. (FIG. 10*c*) Gating (left) and frequency (right) of splenic ILC2s following rIL33 treatment in orthotopic PDAC mice. (FIG. 10*d*) Gating (left) and frequency (right) of tumor ILC2s following rIL33 treatment in subcutaneous PDAC mice. (FIG. 10*e*) Gating (left) and frequency (right) of cytokine and PD-1 expression on tumor CD8$^+$ T cells following rIL33 treatment in orthotopic PDAC mice. (FIG. 10*f*) Frequency of immune cells in vehicle- and rIL33-treated orthotopic PDAC mice. (FIG. 10*g*) Gating strategy for identification of CD103 dendritic cells. (FIG. 10*h*) Gating (left; tumors) and frequency (right) of ILC2s in tumors and draining lymph nodes (DLN) of wild type (WT) or Rora$^{fl/fl}$ IL7r$^{Ce}$ mice (ILC2-deficient) PDAC mice following rIL33 treatment. (FIG. 10*i*) Gating (left) and frequency (right) of PD-1$^+$ CD8$^+$ T cells in tumors of rIL33-treated WT and Batf3$^{-/-}$ mice. Data were collected at 6 (FIG. 10*a*), 5 (FIG. 10*b*), and 3 (FIG. 10*i*) weeks post tumor implantation. Horizontal bars mark medians. n indicates individual mice analyzed separately in at least two independent experiments with n≥2/group. P values determined by two-tailed Mann-Whitney test (FIG. 10*a, f, i*).

FIG. 11*a-c*: Single-cell RNA sequencing of tumor and draining lymph node ILC2s in PDAC mice. (FIG. 11*a*) Experimental design for in vivo treatment, purification, and single-cell analysis of ILC2s. (FIG. 11*b, c*) Quality metrics. (FIG. 11*b*) Scatter plots showing, for each cell, the relationship between the number of unique molecular identifiers (# of UMIs) and the number of genes (# of genes). (FIG. 11*c*) Violin plots showing the distribution of the number of genes (left), number of UMIs (middle), and percentage of normalized reads from mitochondrial genes (right) in each treatment group (columns), and each tissue (rows). Each dot represents a single cell. For each treatment group and organ, data represent pooled purified single cells from biological replicates of n=10 (vehicle), n=5 (rIL33), and n=5 (αPD-1+rIL33) PDAC mice.

FIG. 12*a-f*: Activated ILC2s from tumors and draining lymph nodes have distinct transcriptional features. (FIG. 12*a*) Single-cell analysis of 1,634 rIL33-activated tumor and draining lymph node (DLN) ILC2s (experimental design as outlined in FIG. 11*a*). UMAP plots show single cells (dots) in a nonlinear representation of the top 15 principal components. Expression of (FIG. 12*a*) ILC2 (Gata3, Id2, Rora), and ILC3 (gene, Rorc; protein, Rorγt) transcription factors (TFs), (FIG. 12*b*) ILC2 surface markers, and (FIG. 12*c*) of clusters and organs. Expression of ILC-1 TF Tbx21 (T-bet) was undetectable. (FIG. 12*d, e*) Differentially expressed genes by (FIG. 12*d*) cluster and (FIG. 12*e*) organ (TILC2s and DLN ILC2s). (FIG. 12*f*) Distribution of ('c/5 expression from ILC2s in tumor and DLNs; violin plots show distribution with minima, maxima, and circle indicating median. Each dot in FIG. 12*a* and FIG. 12*b* represents a single cell. For each treatment group and organ, data represent pooled purified single cells from biological replicates of n=5 rIL33-treated PDAC mice. P values by two-sided pairwise Wilcoxon rank sum test.

FIG. 13*a-i*: Combined αPD-1 and rIL33 treatment induces a unique transcriptional profile in tumor ILC2s. (FIG. 13*a*) Expression of coinhibitory immune checkpoints in tumor ILC2s in vehicle-treated PDAC mice by single-cell RNA sequencing (scRNA-seq). (FIG. 13*b*) Gating and frequency of PD-1$^+$ ILC2s in vehicle- and rIL33-treated PDAC mice. DLN, draining lymph node. (FIG. 13*c*) ILC2 frequency in treated PDAC mice. Corresponding tumor volumes, weight, cell number, and scRNA-seq are shown in FIG. 4*a-c*. (FIG. 13*d*) scRNA-seq of ILC2s from treated PDAC mice. Expression of ILC 1 (gene, Tbx21; protein, Tbet), ILC2 (Gata3, Id2, Rora), and ILC3 (gene, Rorc; protein, Rorγt) transcription factors (TFs) in purified tumor and draining lymph node (DLN) ILC2s. Corresponding UMAP plots by cluster and treatment are depicted in FIG. 4*c*. Top differentially expressed genes by treatment and tissue (FIG. 13*e*), cluster (FIG. 13*f*), and distribution of expression for select differentially expressed genes by treatment and tissue (FIG. 13*g*) (tumor: vehicle n=28, rIL33 n=752, rIL33+PD-1 n=2,635; DLN rIL33 n=882, rIL33+PD-1 n=2,725). (FIG. 13*h*) UMAP plots of 3,387 single tumor ILC2s in a non-linear representation of the top 15 principal components. (FIG. 13*i*) Differentially expressed genes in tumor ILC2s by treatment. Each dot in FIG. 13*d* and FIG. 13*h* represents a single cell; for each treatment group and organ, data represent pooled purified single cells from biological replicates of n=10 (vehicle), n=5 (rIL33), and n=5 (αPD-1+rIL33) PDAC mice. Violin plots show distribution with minima, maxima, and circle indicating median. Horizontal bars in FIG. 13*b* and FIG. 13*c* mark medians. P values by two-tailed Mann-Whitney test (FIG. 13*b, c*) and two-sided pairwise Wilcoxon rank sum test (FIG. 13*g*).

FIG. 14*a-g*: Activated tumor ILC2s express PD-1 and co-exist with PD-1$^+$ T cells. Orthotopic PDAC mice (C57Bl/6 WT, Pdcd1$^{-/-}$, CD45.1) were treated with 500 ng of carrier-free recombinant murine IL33 daily for 10 days (experimental designs shown in FIG. 4*e, f*). Live, CD45$^+$, lineage$^-$, CD90$^+$, CD25$^+$, ST2$^+$ tumor ILC2s (TILC2s) were sort-purified to 98% purity at day 10 post-implantation. 5×10$^5$ TILC2s were immediately transferred to orthotopic PDAC tumor-bearing Il7r$^{Cre/+}$ Rora$^{fl/fl}$ (ILC2-deficient) CD45.2 mice on days 7 and 14 post-tumor implantation via i.p. injection. Control mice received equivalent volumes of PBS via i.p. injections. (FIG. 14*a*) Representative plots for TILC2 sort-purification (top) and post-sort purity (bottom). (FIG. 14*b*) Representative plots showing PD-1 expression on sort-purified TILC2s from WT and CD45.1 mice in the experimental designs as outlined in FIG. 4*e, f*. (FIG. 14*c*) Survival and intratumoral CD8$^+$ T cell frequency of orthotopic KPC 4662-GFP and KPC 52 PDAC tumors; horizontal bars in c mark medians. (FIG. 14*d*) Frequency of PD-1$^+$ ILC2s (left) and correlation with PD-1$^+$ T cells (right) in human PDAC. (FIG. 14*e*) Linear regression analysis of IL33 and PD-1 mRNA in bulk tumor transcriptomes of short- and long-human PDAC survivors (left) and survival association of PD-1$^+$ cells in tumor tissue microarrays of short-term and long-term PDAC survivors (right); high and low defined as higher or lower than the median for the cohort. (FIG. 14*f*) Model linking the IL33-TILC2 axis to T cell immunity in pancreatic cancer. (FIG. 14*g*) Distribution of expression of costimulatory molecules in untreated tumor ILC2s by single-cell RNA sequencing. Experimental design as shown in FIG. 11*a*; data represent pooled purified single cells from biological replicates of n=10 (vehicle). Data are representative of purity and PD-1 expression on sorted TILC2s in two independent experiments with n≥4/group (FIG. 14*a, b*). n and data points denote individual mice and patients analyzed separately. P values were determined by two-tailed Mann-Whitney (FIG. 14*c*), and two-sided log rank (FIG. 14*c, e*, survival curves) tests, and linear regression (FIG. 14*d, e*).

DETAILED DESCRIPTION

While some of the main embodiments of the present invention are described in the above Summary of the Invention and in the Examples and Claims sections of this patent application, this Detailed Description section provides certain additional description relating to the compositions and methods of the present invention, and is intended to be read in conjunction with all other sections of the present patent application.

Definitions and Abbreviations

As used in this specification and the appended claims, the singular forms "a," "an," and "the" include plural referents, unless the context clearly dictates otherwise. The terms "a" (or "an") as well as the terms "one or more" and "at least one" can be used interchangeably.

Furthermore, "and/or" is to be taken as specific disclosure of each of the two specified features or components with or without the other. Thus, the term "and/or" as used in a phrase such as "A and/or B" is intended to include A and B, A or B, A (alone), and B (alone). Likewise, the term "and/or" as used in a phrase such as "A, B, and/or C" is intended to include A, B, and C; A, B, or C; A or B; A or C; B or C; A and B; A and C; B and C; A (alone); B (alone); and C (alone).

Units, prefixes, and symbols are denoted in their Système International de Unites (SI) accepted form. Numeric ranges provided herein are inclusive of the numbers defining the range.

Where a numeric term is preceded by "about" or "approximately," the term includes the stated number and values ±10% of the stated number.

Numbers in parentheses or superscript following text in this patent disclosure refer to the numbered references provided in the "Reference List" section at the end of this patent disclosure.

Wherever embodiments are described with the language "comprising," otherwise analogous embodiments described in terms of "consisting of" and/or "consisting essentially of" are included.

As used herein the abbreviation "IL33" refers to interleukin 33.

As used herein the abbreviation "rIL33" refers to recombinant interleukin 33.

As used herein the abbreviation "PDAC" refers to pancreatic ductal adenocarcinoma.

As used herein the abbreviation "ILC2" refers to group 2 innate lymphoid cells.

As used herein the abbreviation "TILC2" refers to tumor ILC2s. It should be noted that all of the embodiments described herein that refer to ILC2s are also intended to encompass TILC2s, and that for all of the methods described herein as involving ILC2s, alternatives that are directed to TILCs-specifically are also contemplated by the present invention.

As used herein the abbreviation "PDX" refers to a patient-derived xenograft.

As used herein the abbreviation PD-1" refers to Programmed Death 1, which is also known as Programmed Death Protein 1 or Programmed Cell Death Protein 1.

As used herein the abbreviation PD-L1 refers to Programmed Cell Death Ligand 1-which is a ligand for PD-1.

As used herein the abbreviation "IP" or "i.p." refers to intraperitoneal. It is common to administer agents to mice via an IP route, which is considered to be analogous to administering an agent to a human subject by an IV route.

As used herein the abbreviation "IT" refers to intratumoral. For example, a drug injected directly into a tumor is delivered intratumorally.

As used herein the abbreviation "IV" refers to intravenous.

As used herein the terms "inhibiting" and "blocking" are used interchangeably, as are the terms "inhibit" or "block" and the terms "inhibitor" or "blocker." The terms "inhibit" and "block" refer to any detectable and statistically significant decrease in a given biological activity.

As used herein the term "allogeneic" refers to deriving from, originating in, or being members of the same species, where the members are genetically related or genetically unrelated but genetically similar. An "allogeneic transplant" or "allogeneic cell therapy" refers to administration of cells obtained from a donor (or derived from cells obtained from a donor) to a recipient, wherein the recipient is the same species as the donor. In embodiments of the present invention involving administration of allogeneic pancreatic ILC2 cells to a subject, the allogeneic cells are obtained from a donor of the same species as the subject to whom the cells will be administered (i.e. the recipient). In some embodiments the allogeneic cells are obtained from a donor having the same MHC/HLA type as the subject to whom the cells will be administered (i.e. the recipient)—i.e. the donor of the cells and the recipient of the cells are MHC-matched or HLA-matched. In some embodiments, cells (e.g. pancreatic ILC2 cells) are: (a) obtained from a donor, (b) maintained and/or cultured and/or expanded and/or activated (e.g. with IL33) ex vivo in vitro, and (c) subsequently administered into a subject of the same species as the donor. For example, in some embodiments, pancreatic ILC2 cells are obtained from a donor, activated with IL33 ex vivo in vitro, and then administered to a recipient subject of the same species as the donor. Such methods can be referred to as allogeneic transplant or transfer or cell therapy methods and the donors or cells obtained from the donors may be referred to as being allogeneic with respect to the recipient. Similarly, in some embodiments, ILC2 cells are obtained from a donor, activated with IL-33 ex vivo in vitro, and then administered to a recipient subject of the same species and same MHC/HLA type as the donor.

As used herein the term "autologous" refers to deriving from or originating in the same subject (i.e. the same individual). An "autologous transplant" or "autologous cell therapy" refers to administration of cells obtained from a donor (or derived from cells obtained from a donor) to a recipient, wherein the donor and the recipient are the same individual. In some embodiments the methods of the present invention involve administering autologous pancreatic ILC2s to a subject, wherein the pancreatic ILC2s are obtained from the same individual/subject to whom the pancreatic ILC2s will be administered (i.e. the donor and recipient are the same individual). In some embodiments, pancreatic ILC2s are: (a) obtained from a subject, (b) maintained and/or cultured and/or expanded and/or activated ex vivo in vitro, and (c) subsequently administered to the same subject. For example, in some such embodiments, pancreatic ILC2s are obtained from a subject, activated with IL33 ex vivo in vitro, and then administered to the same subject. Such methods can be referred to as autologous transplant or transfer or cell therapy methods and the donors or cells obtained from the donors may be referred to as being autologous with respect to the recipient.

As used herein the term "substantially pure" when used in reference to a cell population refers to a population of cells having a specified cell marker characteristic/profile that is at least about 50%, preferably at least about 75-80%, more preferably at least about 85-90%, and most preferably at least about 95% of the cells making up the total cell population. Thus, a "substantially pure" cell population contains fewer than about 50%, preferably fewer than about 20-25%, more preferably fewer than about 10-15%, and most preferably fewer than about 5% of cells that do not display a specified marker characteristic/profile.

As used herein the term "sorting" as it pertains to cells refers to separation of cells based on physical characteristics or presence of markers (such as sorting using side scatter (SSC) and/or forward scatter (FSC), or fluorescence activated cell sorting (FACS) e.g. using labeled antibodies).

As used herein the term "isolated" as it pertains to cells refers to a specified cell type that is separated from at least one other cell type, such as another cell type with which the specified cell type co-exists in nature—e.g. in the body.

Other abbreviations and definitions may be provided elsewhere in this patent specification, or may be well known in the art.

Active Agents

The methods and compositions provided by present invention involve various different active agents, including, but not limited to, IL33 and PD-1 inhibitors.

In those embodiments of the present invention that involve IL33, any suitable IL33 molecule can be used. In preferred embodiments the IL33 molecule used is the IL33 molecule from the species to which the IL33 is to be administered. For example, for administration to humans, human IL33 is used, while for administration to mice, murine IL33 is used. For example, for administration to mice, recombinant murine IL33 (commercially available from R&D Systems, in carrier-containing or carrier-free forms) can be used. Mouse IL33 having the amino acid sequence set forth in UniProtKB/Swiss-Prot: Q8BVZ5.1 can be used. Similarly, for administration to humans, recombinant murine IL33 (commercially available from R&D Systems, in carrier-containing or carrier-free forms) can be used. Human IL33 having the amino acid sequence set forth in UniProtKB/Swiss-Prot: 095760.1 can be used. Other examples of suitable human IL33 sequences that can be used include, but are not limited to, those consisting of or comprising SEQ ID NO. 1 or SEQ ID NO. 2. In some embodiments the IL33 is isolated/purified from animals (e.g. mice, humans) that produce it. In some embodiments the IL33 is recombinantly produced—i.e. it is expressed in any suitable expression system from recombinant DNA encoding IL33. In some embodiments the IL33 is synthetically produced. In some embodiments the IL33 is modified in order to increase or improve its half-life, stability, bioavailability, or to improve any other desired biological property. In some embodiments the IL33 comprises a half-life increasing moiety. Any such modifications known in the art can be used, as long as the modified IL33 retains its ability to bind to, and activate, the IL33 receptor on ILC2 cells. Examples of modifications that can be used include, but are not limited to, pegylation, conjugation to an Fc immunoglobulin domain (such as, for example, SEQ ID NO. 9), conjugation to an albumin-binding domain and hexadecenoic acid modification. Modifications useful for purification or secretion or production of the IL33 may be used, including, but not limited to, expression/purification tags (e.g. His tags, such as SEQ ID NO. 3 or SEQ ID NO. 4), protease recognition sites (e.g. a TEV protease recognition site, such as SEQ ID NO. 5), secretion signals (such as SEQ ID NO. 6), and linker sequences (such as SEQ ID NO. 7 or 8). Examples of modified versions of human IL33 that can be used include, but are not limited to, those consisting of or comprising or produced from SEQ ID NO. 10 (which comprises a His tag and a TEV protease recognition site), SEQ ID NO. 11 (which comprises a secretion signal, a His tag and a linker), or SEQ ID NO. 12 (which comprises a secretion signal, an IgG4-Fc sequence and a linker). For all instances herein that refer to IL33, the present invention contemplates and encompasses embodiments in which the IL33 consists of or comprises any one of SEQ ID NOS. 1, 2, 10, 11 or 12.

TABLE 1

Example Sequences

| SEQ ID NO. | Description/Name | Sequence |
|---|---|---|
| SEQ ID NO. 1 | Hu IL-33 (112-270) | SITGISPITEYLASLSTYNDQSITFALEDESY EIYVEDLKKDEKKDKVLLSYYESQHPSNESGD GVDGKMLMVTLSPTKDFWLHANNKEHSVELHK CEKPLPDQAFFVLHNMHSNCVSFECKTDPGVF IGVKDNHLALIKVDSSENLCTENILFKLSET |
| SEQ ID NO. 2 | IL33 (aa111-270) | SSITGISPITEYLASLSTYNDQSITFALEDES YEIYVEDLKKDEKKDKVLLSYYESQHPSNESG DGVDGKMLMVTLSPTKDFWLHANNKEHSVELH KCEKPLPDQAFFVLHNMHSNCVSFECKTDPGV FIGVKDNHLALIKVDSSENLCTENILFKLSET |
| SEQ ID NO. 3 | His Tag | HHHHHHHH |
| SEQ ID NO. 4 | His Tag | HHHHHH |
| SEQ ID NO. 5 | TEV protease recognition site | ENLYFQG |
| SEQ ID NO. 6 | Secretion signal | MGWSCIILFLVATATGVHS |
| SEQ ID NO. 7 | Linker | GGGG |
| SEQ ID NO. 8 | Linker | *GGGGSGGGG* |
| SEQ ID NO. 9 | hIgG4-Fc | DKRVESKYGPPCPPCPAPEFLGGPSVFLFPPK PKDTLMISRTPEVTCVVVDVSQEDPEVQFNWY VDGVEVHNAKTKPREEQFNSTYRVVSVLTVLH QDWLNGKEYKCKVSNKGLPSSIEKTISKAKGQ PREPQVYTLPPSQEEMTKNQVSLTCLVKGFYP SDIAVEWESNGQPENNYKTTPPVLDSDGSFFL YSRLTVDKSRWQEGNVFSCSVMHEALHNHYTQ KSLSLSLGK |
| SEQ ID NO. 10 | His-TEV Hu IL-33 (112-270) | MS**HHHHHHHH*ENLYFQG*S**ITGISPITEYLA SL̲S̲T̲Y̲N̲D̲Q̲SITFALEDESYEIYVEDLKKDEKK DKVLLSYYESQHPSNESGDGVDGKMLMVTLSP TKDFWLHANNKEHSVELHKCEKPLPDQAFFVL HNMHSNCVSFECKTDPGVFIGVKDNHLALIKV DSSENLCTENILFKLSET Bold & underlined is His-tag Bold & italicized is TEV protease recognition site |

TABLE 1-continued

Example Sequences

| SEQ ID NO. | Description/Name | Sequence |
|---|---|---|
| SEQ ID NO. 11 | Secretion signal-His-linker-IL33 (aa111-270) | MGWSCIILFLVATATGVHS*HHHHHH**GGGGSS*<br>ITGISPITEYLASLSTYNDQSITFALEDESYE<br>IYVEDLKKDEKKDKVLLSYYESQHPSNESGDG<br>VDGKMLMVTLSPTKDFWLHANNKEHSVELHKC<br>EKPLPDQAFFVLHNMHSNCVSFECKTDPGVFI<br>GVKDNHLALIKVDSSENLCTENILFKLSET<br>Bold & underlined is secretion signal<br>Bold & italic is H-tag<br>Italic is linker |
| SEQ ID NO. 12 | Secretion signal-hIgG4-Fc (S228P)-linker-IL33 | MGWSCIILFLVATATGVHS*DKRVESKYGP*<br>*PCPPCPAPEFLGGPSVFLFPPKPKDTLMISR*<br>*TPEVTCVVVDVSQEDPEVQFNWYVDGVEV*<br>*HNAKTKPREEQFNSTYRVVSVLTVLHQDWL*<br>*NGKEYKCKVSNKGLPSSIEKTISKAKGQPRE*<br>*PQVYTLPPSQEEMTKNQVSLTCLVKGFYPS*<br>*DIAVEWESNGQPENNYKTTPPVLDSDGSFF*<br>*LYSRLTVDKSRWQEGNVFSCSVMHEALHN*<br>*HYTQKSLSLSLGK*GGGGSGGGGSSSITGISPIT<br>EYLASLSTYNDQSITFALEDESYEIYVEDLKK<br>DEKKDKVLLSYYESQHPSNESGDGVDGKMLMV<br>TLSPTKDFWLHANNKEHSVELHKCEKPLPDQA<br>FFVLHNMHSNCVSFECKTDPGVFIGVKDNHLA<br>LIKVDSSENLCTENILFKLSET<br>Bold & underlined is secretion signal<br>Bold & italic is IgG4-Fc sequence<br>Italic is linker |
| SEQ ID. NO. 13 | Optimized nucleotide sequence encoding His-TEV Hu IL-33 (112-270) | ATGTCCCACCATCACCATCACCACCACCACGA<br>AAATCTGTACTTCCAAGGCAGCATCACCGGCA<br>TCAGCCCCATCACCGAGTATCTGGCCTCTCTG<br>TCCACCTACAACGACCAGTCCATCACATTCGC<br>TCTGGAGGACGAAAGCTACGAGATCTACGTGG<br>AGGATCTGAAGAAGGACGAGAAGAAGGACAAG<br>GTGCTGCTGTCCTACTACGAGTCCCAGCACCC<br>CTCCAACGAAAGCGGCGACGGCGTGGATGGCA<br>AGATGCTGATGGTGACACTGAGCCCCACCAAG<br>GACTTTTGGCTGCACGCCAACAACAAGGAGCA<br>CAGCGTGGAGCTGCACAAGTGCGAGAAACCTC<br>TGCCCGACCAAGCCTTCTTCGTGCTGCACAAC<br>ATGCACAGCAACTGCGTGTCCTTCGAGTGCAA<br>GACCGACCCCGGCGTGTTCATCGGCGTGAAGG<br>ACAACCATCTGGCTCTGATCAAGGTGGACAGC<br>TCCGAGAACCTCTGCACCGAGAACATTCTGTT<br>CAAGCTGTCCGAGACCTGATGA |
| SEQ ID NO. 14 | Optimized nucleotide sequence encoding His-TEV Hu IL-33 (112-270)-with added restriction sites | <u>AAGCTT</u>ATGTCCCACCATCACCATCACCACCA<br>CCACGAAAATCTGTACTTCCAAGGCAGCATCA<br>CCGGCATCAGCCCCATCACCGAGTATCTGGCC<br>TCTCTGTCCACCTACAACGACCAGTCCATCAC<br>ATTCGCTCTGGAGGACGAAAGCTACGAGATCT<br>ACGTGGAGGATCTGAAGAAGGACGAGAAGAAG<br>GACAAGGTGCTGCTGTCCTACTACGAGTCCCA<br>GCACCCCTCCAACGAAAGCGGCGACGGCGTGG<br>ATGGCAAGATGCTGATGGTGACACTGAGCCCC<br>ACCAAGGACTTTTGGCTGCACGCCAACAACAA<br>GGAGCACAGCGTGGAGCTGCACAAGTGCGAGA<br>AACCTCTGCCCGACCAAGCCTTCTTCGTGCTG<br>CACAACATGCACAGCAACTGCGTGTCCTTCGA<br>GTGCAAGACCGACCCCGGCGTGTTCATCGGCG<br>TGAAGGACAACCATCTGGCTCTGATCAAGGTG<br>GACAGCTCCGAGAACCTCTGCACCGAGAACAT<br>TCTGTTCAAGCTGTCCGAGACCTGATGA<br>*GCGGCCGC*<br>HindIII restriction site-bold &<br>underlined<br>NotI restriction site-bold,<br>underlined & italic |

In those embodiments of the present invention that involve PD-1 inhibitors, any suitable PD-1 inhibitor known in the art may be used. In some embodiments the PD-1 inhibitor is an antibody. In some embodiments the PD-1 inhibitor is selected from the group consisting of: Pembrolizumab (Keytruda, Merck), Nivolumab (Opdivo, Bristol-Myers Squibb), Cemiplimab (Libtayo, Regeneron), AMP-224 (GlaxoSmithKline), AMP-514 (GlaxoSmithKline), and PDR001 (Novartis).

In those embodiments of the present invention that involve PD-L1 inhibitors, any suitable PD-L1 inhibitor known in the art may be used. In some embodiments the PD-L1 inhibitor an antibody. In some embodiments the PD-L1 inhibitor is selected from the group consisting of Atezolizumab (Tecentriq, Roche Genentech), Avelumab (Bavencio, Merck Serono and Pfizer), Durvalumab (Imfinzi, AstraZeneca), BMS-936559 (Bristol-Myers Squibb), CK-301 (Checkpoint Therapeutics).

Many of the embodiments of the present invention described above and/or elsewhere herein involve the use of a PD-1 and/or PD-L1 inhibitor. It should be noted that in all cases, the present invention also includes the same embodiments with the variation that only a PD-1 inhibitor is used.

In some embodiments, the methods of the present invention can be carried out using analogues, homologues, variants, or derivatives that are equivalents of any of the specific active agents described herein. Such analogues, homologues, variants, or derivatives should retain the key functional properties of the specific molecules described herein. For example, in the case of PD-1 and/or PD-L1 inhibitors, any suitable analogue, homologue, variant, or derivative of such an agent can be used provided that it retains PD-1 and/or PD-L1 inhibitory activity. In the case of IL33, any suitable analogue, homologue, variant, or derivative of such an agent can be used provided that it retains the ability to bind to, and activate, IL33 receptors on ILC2 cells.

In certain embodiments, the present invention provides compositions comprising at least one active agent as described herein, and one or more other components useful in formulating a composition for delivery to a subject, such as diluents, buffers, carriers, stabilizers, dispersing agents, suspending agents, thickening agents, excipients, preservatives, and the like.

Methods of Treatment

The present invention provides various methods of treatment. For example, in some embodiments the present invention provides treatment methods that comprise administering effective amounts of one or more of the active agents described herein (e.g. IL33 and/or a PD-1 and/or PD-L1 inhibitor) to subjects in need thereof. The present invention also provides various methods of activating ILC2 cells in a pancreatic tumor (e.g. in a PDAC tumor). These methods also generally comprise administering effective amounts of one or more of the active agents described herein (e.g. IL33 and/or a PD-1 and/or PD-L1 inhibitor) to subjects in need thereof. In some embodiments the present invention also provides various cell therapy methods. These cell therapy methods involve administering to a recipient subject with PDAC an effective amount of activated donor pancreatic ILC2 cells that have been obtained from a donor subject and activated ex vivo in vitro by contact with IL33.

As used herein, the terms "treat," "treating," and "treatment" encompass achieving, and/or performing a method that achieves, a detectable improvement in one or more clinical indicators or symptoms associated with pancreatic cancer (e.g. PDAC). For example, such terms include, but are not limited to, reducing the rate of growth of a pancreatic tumor (or of pancreatic tumor cells), halting the growth of a pancreatic tumor (or of pancreatic tumor cells), causing regression of a pancreatic tumor (or of pancreatic tumor cells), reducing the size of a pancreatic tumor (for example as measured in terms of tumor volume or tumor mass), reducing the grade of a pancreatic tumor, eliminating a pancreatic tumor (or pancreatic tumor cells), preventing, delaying, or slowing recurrence (rebound) of a pancreatic tumor, improving symptoms associated with a pancreatic tumor, improving survival from a pancreatic tumor, inhibiting or reducing spreading of a pancreatic tumor (e.g. metastases), and the like. In each of the embodiments described herein that refer to a method of treatment, a method of achieving any one or more of the specific parameters listed above is also contemplated. For example, for each of the embodiments described herein that refers to a method of treating pancreatic cancer (e.g. PDAC), the following methods are also contemplated and are intended and fall within the scope of the invention: (a) a method of reducing the rate of growth of a pancreatic tumor (or of pancreatic tumor cells), (b) a method of halting the growth of a pancreatic tumor (or of pancreatic tumor cells), (c) a method of causing regression of a pancreatic tumor (or of pancreatic tumor cells), (d) a method of reducing the size of a pancreatic tumor (for example as measured in terms of tumor volume or tumor mass), (e) a method of reducing the grade of a pancreatic tumor, (f) a method of eliminating a pancreatic tumor (or pancreatic tumor cells), (g) a method of preventing, delaying, or slowing recurrence (rebound) of a pancreatic tumor, (h) a method of improving symptoms associated with a pancreatic tumor, (i) a method of improving survival from a pancreatic tumor, and (j) a method of inhibiting or reducing spreading of a pancreatic tumor (e.g. metastasis).

As used herein the term "subject" encompasses all mammalian species, including, but not limited to, humans, non-human primates, dogs, cats, rodents (such as rats, mice and guinea pigs), cows, pigs, sheep, goats, horses, and the like-including all mammalian animal species used in animal husbandry, as well as animals kept as pets and in zoos, etc. In some embodiments the subjects are human.

In some embodiments the present methods and compositions can be used to treat any pancreatic tumor in a subject in need thereof (i.e. a subject with pancreatic cancer). In preferred embodiments the present methods and compositions are used to pancreatic ductal adenocarcinoma (PDAC) in a subject in need thereof (i.e. a subject with PDAC). In some embodiments the present methods and compositions are used to treat PD-1/PD-L1 inhibitor resistant PDAC in a subject in need thereof (i.e. a subject with PD-1 and/or PD-L1 inhibitor resistant PDAC).

In some embodiments the subject has a tumor that is resistant to treatment using other methodologies and/or compositions. As used herein, the terms "resistant" and "resistance" are used consistent with their normal usage in the art and consistent with the understanding of those term by physicians who treat cancer (e.g. oncologists). For example, consistent with its usual meaning in the art, a tumor or a subject may be considered "resistant" to a certain treatment method or treatment with a certain agent (or combination of agents), if, despite using that method or administering that agent (or combination of agents), a subject's tumor (or tumor cells) grows, and/or progresses, and/or spreads, and/or metastasizes, and/or recurs. In some instances, a tumor may initially be sensitive to treatment with a certain method or agent (or combination of agents), but later became resistant to such treatment.

In some embodiments the subject has a pancreatic tumor (e.g. PDAC) that has recurred following a prior treatment with other compositions or methods, including, but not limited to, chemotherapy, radiation therapy, or surgical resection, or any combination thereof. In some embodiments the subject has a pancreatic tumor that has not previously been treated.

As used herein the term "effective amount" refers to an amount of an active agent or cells as described herein that is sufficient to achieve, or contribute towards achieving, one or more desirable clinical outcomes, such as those described in the "treatment" description above and/or to activate ILC2 cells in a pancreatic tumor (e.g. in a PDAC tumor). An appropriate "effective" amount in any individual case may be determined using standard techniques known in the art, such as dose escalation studies, and may be determined taking into account such factors as the desired route of administration (e.g. systemic vs. intratumoral), desired frequency of dosing, etc. In some embodiments an "effective amount" may be an amount already found to be effective in a clinical trial and/or approved for administration to human subjects. For example, in some embodiments an effective amount of IL33, a PD-1 inhibitor or a PD-L1 inhibitor may be an amount already shown to be effective in a clinical trial and/or already approved for administration to human subjects. Furthermore, an "effective amount" may be determined in the context of any co-administration method to be used. One of skill in the art can readily perform such dosing studies (whether using single agents or combinations of agents) to determine appropriate doses to use, for example using assays such as those described in the Examples section of this patent application-which involve administration of the agents described herein to subjects (such as animal subjects routinely used in the pharmaceutical sciences for performing dosing studies).

For example, in some embodiments the dose of an active agent of the invention may be calculated based on studies in humans or other mammals carried out to determine efficacy and/or effective amounts of the active agent. The dose may be determined by methods known in the art and may depend on factors such as pharmaceutical form of the active agent, route of administration, whether only one active agent is used or multiple active agents (for example, the dosage of a first active agent required may be lower when such agent is used in combination with a second active agent), and patient characteristics including age, body weight or the presence of any medical conditions affecting drug metabolism.

In those embodiments described herein that refer to specific doses of agents to be administered based on mouse studies, one of skill in the art can readily determine comparable doses for human studies based on the mouse doses, for example using the types of dosing studies and calculations known in the art and/or described herein.

In some embodiments suitable doses of the various active agents described herein can be determined by performing dosing studies of the type that are standard in the art, such as dose escalation studies, for example using the dosages shown to be effective in mice in the Examples section of this patent application as a starting point.

In some embodiments one or more of the active agents is used at approximately its maximum tolerated dose, for example as determined in phase I clinical trials and/or in dose escalation studies. In some embodiments one or more of the active agents is used at about 90% of its maximum tolerated dose. In some embodiments one or more of the active agents is used at about 80% of its maximum tolerated dose. In some embodiments one or more of the active agents is used at about 70% of its maximum tolerated dose. In some embodiments one or more of the active agents is used at about 60% of its maximum tolerated dose. In some embodiments one or more of the active agents is used at about 50% of its maximum tolerated dose. In some embodiments one or more of the active agents is used at about 50% of its maximum tolerated dose. In some embodiments one or more of the active agents is used at about 40% of its maximum tolerated dose. In some embodiments one or more of the active agents is used at about 30% of its maximum tolerated dose.

In carrying out the treatment methods described herein, any suitable method or route of administration can be used to deliver the active agents and/or cells or combinations thereof described herein. In some embodiments systemic administration may be employed, for example, oral or intravenous (IV) administration, or any other suitable method or route of systemic administration known in the art. In some embodiments intratumoral (IT) delivery may be employed. In some embodiments intraperitoneal (IP) delivery may be employed. For example, the active agents described herein may be administered either systemically or locally by injection, by infusion through a catheter, using an implantable drug delivery device, or by any other means known in the art. One of skill in the art will be able to select the appropriate delivery method or route depending on the situation, for example depending on whether active agents or cells are being administered, and in the case of active agents, depending on the nature of the active agent (e.g. its stability, half-life, etc.).

In certain embodiments the compositions and methods of treatment provided herein may be employed together with other compositions and treatment methods known to be useful for tumor therapy, including, but not limited to, surgical methods (e.g. for tumor resection), radiation therapy methods, treatment with chemotherapeutic agents, treatment with antiangiogenic agents, treatment with tyrosine kinase inhibitors or treatment with immune checkpoint inhibitors. Similarly, in certain embodiments the methods of treatment provided herein may be employed together with procedures used to monitor disease status/progression, such as biopsy methods and diagnostic methods (e.g. MRI methods or other imaging methods).

For example, in some embodiments the methods described herein may be performed prior to performing surgical resection of a tumor, for example in order to shrink a tumor prior to surgical resection. In other embodiments the methods described herein may be performed both before and after performing surgical resection of a tumor.

In some embodiments the treatment methods described herein may be employed in conjunction with performing a diagnostic test to determine if the subject has a tumor that that is likely to be responsive to therapy. For example, in some embodiments, prior to commencing treatment, a diagnostic assay is performed to determine if the subject has PDAC, and/or to determine if the subject has a pancreatic cancer (e.g. PDAC) comprising cells that express anIL33 receptor, such as ST2, of that express PD-1 and/or PD-L1.

In the cell therapy-based methods that are described herein, protocols that are used for other types of cell therapy for tumors (e.g. other types of autologous cell therapy for tumors) can readily be adapted for use with ILC2 cells. For example, modifications of TIL therapy methods and CAR-T cell therapy methods can be used—as each of these methods involves obtaining cells from a donor, manipulating those cells in vitro ex vivo in some way, and then subsequently administering those cells to a recipient. For example, methods of obtaining lymphocytes from a donor, isolating/puri-fying those cells, culturing/maintaining/expanding those cells in vitro ex vivo, and administering those cells to recipients, are well known in the art, and modifications of such methods can be used in conjunction with the ILC2-based cell therapies described herein. As regards purifying pancreatic ILC2 cells obtained in a subject, this can be performed using standard cell isolation/purification methods known in the art, such as FACs-based methods. Several ILC2 markers that can be used in such cell isolation/purification methods are described in the Examples section of this patent specification. Other suitable markers are known in the art.

EXAMPLES

The invention is further described by the following non-limiting "Examples" and the Figures referred to therein. The numbers in superscript in the Examples section indicate the numbered references in the Reference List section of this disclosure.

Example 1

Activation of Tissue-Specific Innate Lymphoid Cells Augments PD-1 Checkpoint Blockade Immunotherapy in Pancreatic Cancer Overview Group 2 innate lymphoid cells (ILC2s) regulate inflam-mation and immunity in tissues[1]. Although ILC2s are detected in cancers of these tissues[2], their role in cancer immunity and immunotherapy are unclear. Here, we identify that ILC2s infiltrate pancreatic ductal adenocarcinomas (PDAC) to activate tissue-specific tumor immunity. Inter-leukin-33 (IL33) activates tumor ILC2s (TILC2s) and CD8[+] T cells in orthotopic pancreatic but not heterotopic skin tumors to restrict pancreas-specific tumor growth. Resting and activated TILC2s express the inhibitory checkpoint receptor PD-1, and TILC2s further expand with PD-1 block-ade (αPD-1) to enhance tumor control. PD-1 blockade acts directly on TILC2s to augment anti-tumor immunity and αPD-1 immunotherapy efficacy, identifying activated TILC2s as novel targets of αPD-1. Finally, both PD-1[+] TILC2s and PD-1[+] T cells are present in the majority of human PDACs. Collectively, we identify ILC2s as novel anti-cancer immune cells for PDAC immunotherapy. More broadly, ILC2s emerge as tissue-specific enhancers of cancer immunity that amplify efficacy of αPD-1 immunotherapy. As ILC2s and T cells co-exist in human cancers with shared pathways of activation and inhibition, collective targeting of anti-cancer ILC2s and T cells may be a broadly applicable immunotherapeutic approach.

TILC2s Infiltrate Pancreatic Cancers

In unselected primary human PDACs, we found intratu-moral cells lacking immune cell lineage markers (Lin⁻) but expressing ILC (CD25 and CD127)[1], and ILC2 (IL33-receptor ST2/IL1RL1/IL33R, and GATA3) markers (FIG. 1a, FIG. 5a). These putative TILC2s were enriched in rare long-term PDAC survivors with "hot" tumors (activated CD8[+] T cell enriched)[3] when compared to short-term sur-vivors with cold tumors, and higher TILC2 frequencies correlated with longer survival (FIG. 1b, FIG. 5b). Consis-tently, higher bulk tumor RNA expression of the ILC2-activating cytokine IL33, but no other ILC activating cyto-kine, was associated with longer survival (FIG. 1c, FIG. 5c). Furthermore, IL33, but no other ILC-activating cytokines, correlated with higher intratumoral immune cytolytic activ-ity (FIG. 1c, FIG. 5c). Although these data assess RNA and not protein content, they suggested that IL33 and TILC2s activate anti-tumor immunity in human PDAC.

We next surveyed tumors in mutated Kras and p53-driven autochthonous "KPC" mice[4] and orthotopic PDAC mouse models (PDAC mice[5, 6]) for ILCs. In both models, we detected TILC2s phenotypically similar to those in human PDAC and to murine ILC2s[1, 7] (FIG. 1d, FIG. 5d-f). Murine TILC2s expanded in tumors, but not in adjacent organs (FIG. 1d, FIG. 5g), consistent with their tissue-residency[8], and were depleted in Rag2⁻/⁻ mice[9,10] by targeting the lymphocyte antigen CD90.2 (FIG. 1e, FIG. 5h). Therefore, ILC2s are conserved cells that expand locally in mouse and human PDAC.

In identifying the signals inducing TILC2 expansion, we found that in both PDAC and KPC mice[11] IL33 had the highest expression in tumors when compared to other ILC-inducer cytokines (FIG. 6a)[6], with heterogeneous expres-sion in both human and mouse PDACs (FIG. 6b-c) and maximal expression in intratumoral myeloid cells[12, 13] (FIG. 6d, e). To understand the role of IL33 and TILC2s in PDAC immunity, we studied TILC2 dependencies in IL33$^{High}$ PDAC mice that reflect IL33$^{High}$, ILC2 enriched hot tumors in long-term human PDAC survivors. TILC2 expansion and function was IL33 dependent, as Il33⁻/⁻ PDAC mice had reduced TILC2 frequency, number (FIG. 1f, FIG. 6f), and cytokine production (FIG. 6g) when compared to Il33⁺/⁺ PDAC mice. Consistently, recombinant IL33 (rIL33) expanded ILCs in ILC-proficient Rag2⁻/⁻ PDAC mice, but not in ILC-deficient Rag2⁻/⁻ γ$_c$⁻/⁻ PDAC mice (FIG. 6h, i). Collectively, these experiments demonstrated that IL33 expanded PDAC TILC2s.

TILC2s Boost Tumor Immunity in Tissues

As ILC2s have tissue-specific phenotypes[14], we hypoth-esized that TILC2 effects on PDAC immunity would be tissue-specific. To test this, we contrasted the effects of IL33 deficiency on tumor growth in the pancreas to the skin (pancreatic TILC2s express ST2, skin TILC2s do not; FIG. 6j[14, 15]). Compared with Il33⁺/⁺ animals, Il33⁻/⁻ mice with orthotopic PDAC had larger tumors, accelerated tumor growth, and worse survival (FIG. 6a), in contrast to subcu-taneous PDAC mice that showed no IL33-dependent phe-notype (FIG. 2b, FIG. 6k). Although these mice were fully backcrossed onto identical genetic backgrounds, we con-firmed these differences were not due to potential minor genetic mismatches by observing larger tumors in Il33⁻/⁻ vs. Il33⁺/⁺ littermates (FIG. 6l). These anti-tumor effects were host hematopoietic cell-derived IL33 dependent, as chimeric mice transplanted with Il33⁻/⁻ bone marrow had larger tumors compared to control mice (FIG. 6m-o). RNA sequencing (RNA-seq) of purified CD45⁺ intratumoral immune cells from Il33⁺/⁺ and Il33⁻/⁻ orthotopic PDAC mice revealed Il33⁻/⁻ PDAC immune cells had diminished transcriptional signatures of T cell activation and MHC-I antigen processing, suggesting a T cell priming deficiency (FIG. 7a). Consistently, Il33⁻/⁻ orthotopic but not subcuta-neous PDAC mice had lower frequencies of global and activated tumor-infiltrating CD8⁺ T cells with no consistent changes in other immune cell frequencies, and reduced central memory CD8⁺ T cells (T$_{CM}$) in draining (DLN) but not distant lymph nodes (FIG. 2c, FIG. 7c-e). The increase in tumor size in Il33⁻/⁻ compared to Il33⁺/⁺ mice was abrogated upon pan-T cell depletion (FIG. 2d), with no differences in tumor weight in rIL33-treated Rag2⁻/⁻ PDAC mice (FIG. 8a), confirming the anti-tumor effects of IL33 were T cell mediated. Orthotopic tumors from Il33⁻/⁻ and Il33$^{+/+}$ PDAC mice also had similar histology, collagen, and fibroblast content (FIG. 8b-d), with no effects of rIL33 on tumor cells in vitro (FIG. 8e-g), showing IL33 had no direct effects on tumor or stromal cells. Together, these data demonstrated that IL33 activated tissue-specific cancer immunity by potentially activating TILC2s to prime CD8$^+$ T cells.

We next investigated if the effect of IL33 on CD8$^+$ T cells was tissue specific by contrasting the rejection phenotype of KPC cells expressing the CD8$^+$ T cell rejection antigen ovalbumin (KPC-OVA) at different tissue sites. Interestingly, 70% of Il33$^{+/+}$ mice rejected orthotopic KPC-OVA tumors, whereas 0% of Il33$^{-/-}$ mice did. In contrast, 100% of Il33$^{+/+}$ and Il33$^{-/-}$ mice rejected subcutaneous KPC-OVA tumors (FIG. 2e). To assess if this phenotype resulted from ILC2 deficiency and ineffective CD8$^+$ T cell priming, we acutely depleted ILC2s and examined antigen-specific CD8$^+$ T cells in DLNs using the iCOS-T mouse, which allows diphtheria toxin-mediated ILC2 depletion while sparing ICOS$^+$CD4$^+$ T cells[16] (FIG. 2f, FIG. 9a). ILC2 depletion recapitulated the Il33$^{-/-}$ phenotype, with a higher rate of tumor rejection and larger tumor size in orthotopic KPC-OVA tumors and no differences in subcutaneous tumors (FIG. 2f), with anticipated variation compared to Il33$^{-/-}$ mice given differences in time of rejection assessment and depletion efficacy. Tetramer analysis in ILC2-depleted orthotopic KPC-OVA mice revealed reductions in OVA-specific CD8$^+$ T cells in DLNs and spleens, and reductions in CD8$^+$ $T_{CM}$ in DLNs (as seen in Il33$^{-/-}$ mice) (FIG. 2g, FIG. 9b, c). Therefore, ILC2 deficiency partially phenocopied IL33 deficiency. Although direct effects of IL33 on CD8$^+$ T cells cannot be ruled out, we found no ST2 expression on intratumoral CD8$^+$ T cells (FIG. 9d). To summarize, these loss-of-function experiments suggested that the IL33-TILC2 axis primes tissue-specific CD8$^+$ T cell PDAC immunity.

Next, to examine if rIL33 treatment had similar tissue-specific anti-tumor effects, we found rIL33 prevented tumor establishment in orthotopic PDAC mice and prolonged survival, with no effects on subcutaneous PDAC mice, leading to progressive tumor growth and ulceration requiring euthanasia (FIG. 3a), with similar tissue-specific anti-tumor effects in KPC-OVA PDAC mice (FIG. 10a). Similarly, rIL18, a cytokine that preferentially activates IL18R$^+$ skin ILC2s[14], restricted the growth of subcutaneous PDACs infiltrated by IL18R$^+$ ILCs, but not orthotopic PDACs that lack IL18R$^+$ ILCs (FIG. 3b, FIG. 10b). rIL33 selectively expanded ILC2s in DLNs and tumors of orthotopic PDAC mice (FIG. 3c), with no changes in the spleen or in subcutaneous PDACs (FIG. 10c, d). ILC2 expansion was accompanied by enhanced intratumoral CD8$^+$ T cell cytokine capacity and PD-1 upregulation (FIG. 10e), with no consistent changes in other intratumoral immune cells (FIG. 10f), although potential modulation of their function cannot be ruled out. Consistent with ILC2s priming anti-tumor CD8$^+$ T cells indirectly, rIL33 treatment doubled intratumoral CD103$^+$ dendritic cells (DCs) (FIG. 3d, FIG. 10g) which prime and recruit CD8$^+$ T cells into PDACs[6]. To determine if the effects of rIL33 depended on ILC2s, we administered rIL33 to PDAC-bearing Rora$^{fl/fl}$ Il17r$^{Cre/+}$ mice constitutively deficient in ILC2s.[16] ILC2 deficiency (FIG. 10h) abrogated rIL33 efficacy (FIG. 3e) and attenuated increases in CD103 DCs in tumors (FIG. 3f). rIL33 also had no anti-tumor effects (FIG. 3g) and failed to induce intratumoral CD8$^+$ T cell PD-1 expression (FIG. 10i) in CD103$^+$ DC-deficient Batf3$^{-/-}$ mice, establishing that CD103$^+$ DCs were essential for rIL33-mediated tumor control. To identify if TILC2s produced chemokines to recruit DCs into tumors, we used single-cell RNA-seq (scRNA-seq) (FIG. 11a-c) and found activated TILC2s and DLN ILC2s retained markers of ILC2 identity but exhibited distinct transcriptional profiles (FIG. 12a-e), with rIL33-activated TILC2s selectively expressing Ccl5 (FIG. 12f), which encodes a chemokine that recruits CD103$^+$ DCs into tumors[17], and induced efficient DC migration in vitro (FIG. 3h). In sum, these data suggested that rIL33 expands TILC2s to recruit CD103$^+$ DCs into tumors, potentially through Ccl5 production, and activate CD8$^+$ T cells to induce therapeutic tumor immunity.

PD-1 Blockade Activates TILC2s

As stimulating ILC2s with rIL33 had anti-tumor effects, we searched for strategies to further boost ILC2 activation. Recent data have shown that, like T cells, ILC2s regulate their activity through coinhibitory[2, 18] immune checkpoint pathways. Specifically, the immune checkpoint PD-1 regulates mouse ILC2 development[19], marks effector ILCs[19], and when genetically deficient or inhibited with a blocking antibody (αPD-1), IL33-activated ILC2s show greater expansion and effector function in mice and humans[20]. PD-1$^+$ILC2s are also found in human tumors[2]. Yet, concurrent ILC2 activation and disinhibition for cancer therapy is relatively unexplored.

Using scRNA-seq (FIG. 11a-c), we found PD-1 was the only detectable coinhibitory molecule expressed at baseline by TILC2s (FIG. 13a). rIL33 treatment upregulated PD-1 on a fraction of TILC2s but not in DLN ILC2s (FIG. 13b), suggesting PD-1 may functionally restrain activated TILC2s. We therefore explored if combining rIL33 with αPD-1 could cooperatively activate TILC2s to enhance anti-tumor efficacy. Consistent with PD-1 expression only on rIL33-activated TILC2s, αPD-1 alone induced a partial response (FIG. 4a) as previously reported in PDACs[6] but did not appreciably alter TILC2 frequencies (FIG. 4b, FIG. 13c). Combining rIL33 with αPD-1 maximally expanded ILC2s in tumors and DLNs (FIG. 4b) and enhanced tumor control compared to αPD-1 alone (FIG. 4a). To explore if αPD-1 was activating ILC2s by cell-intrinsic PD-1 blockade, we compared the single-cell transcriptional profiles of TILC2s and DLN ILC2s following in vivo treatment. While TILC2s retained transcriptional and cellular identities of ILC2s irrespective of treatment (FIG. 13d), TILC2s in rIL33 and αPD-1 treated PDAC mice had unique transcriptional phenotypes compared to all other conditions (FIG. 4c), with increased expression of ILC2-specific markers, canonical (amphiregulin [Areg]) 14 and non-canonical (CXCL2)[21] effector molecules, cellular activation machinery (Junb, Fosl2, Ybx1), and coinhibitory immune checkpoints (FIG. 13e-i). Finally, the anti-tumor effects of dual therapy were abrogated in ILC2-deficient mice (FIG. 4d), demonstrating that ILC2s were necessary for the efficacy of dual αPD-1 and rIL33 therapy. These results suggested αPD-1 preferentially amplified activated TILC2s by possibly inhibiting the PD-1 pathway on ILC2s, and not exclusively on T cells.

PD-1 TILC2 Inhibition is Cell-Intrinsic

To identify if cell-intrinsic PD-1 pathway interruption on activated TILC2s contributed to the anti-tumor effects of dual therapy, we transferred sort-purified rIL33-activated PD-1-proficient (wild-type [WT]) or PD-1 deficient (Pdcd1$^{-/-}$) TILC2s into tumor-bearing ILC2-deficient mice (FIG. 4e, FIG. 14a). WT TILC2 transfer had no anti-tumor efficacy in established tumors, but Pdcd1$^{-/-}$ TILC2s restricted tumor growth, indicating that interrupting PD-1 signaling on TILC2s can enhance tumor control (FIG. 4e). We next tested if rIL33-activated PD-1$^+$ TILC2s can directly amplify the efficacy of αPD-1 therapy in established tumors.

We transferred sort-purified rIL33-activated congenic CD45.1$^+$ TILC2s into CD45.2$^+$ ILC2-deficient mice with established tumors, and treated with αPD-1 post-transfer (FIG. 4$f$). Transferred TILC2s were >97% PD-1$^+$ (FIG. 10$b$) and accumulated in tumors and DLNs, but not spleens, of αPD-1 treated recipient mice, persisting up to 9 weeks post transfer (FIG. 4$g$). PD-1$^+$ TILC2 transfer augmented αPD-1 efficacy, restricted tumor growth, and increased T cell frequencies in tumors and DLNs, but not spleens, of recipient mice (FIG. 4$h$). These data collectively demonstrated that blockade of PD-1 signaling on rIL33-activated TILC2s had direct anti-tumor effects and amplified αPD-1 efficacy.

To examine rIL33 and αPD-1 efficacy in IL33$^{Low}$ αPD-1-resistant tumors, we selected an aggressive "cold" PDAC model (KPC 52) that generates IL33$^{Low}$ tumors (FIG. 6$b$), has 50% fewer CD8$^+$ T cells, and has a median survival of only 2 weeks (FIG. 14$c$), to mimic the immunologic and survival features of IL33$^{Low}$ short-term human PDAC survivors. Although KPC 52 PDAC mice do not exhibit the sequential steps of PDAC tumorigenesis from pre-invasive neoplasias to invasive PDAC as seen in spontaneous KPC mice, they recapitulated the αPD-1 resistance seen in spontaneous KPC mice and human PDAC (FIG. 4$i$). We found that combination rIL33 and αPD-1 reduced tumor volume by nearly 40%, with a nearly 50% improvement in mouse survival (FIG. 4$i$). Finally, to assess the potential to treat PDAC patients with dual rIL33 and αPD-1 therapy, we found nearly 60% of human PDACs had low frequencies of PD-1$^+$ TILC2s and PD-1$^+$ T cells, with a significant correlation between the two cell types (FIG. 14$d$), suggesting they frequently co-occur in human PDAC. Additionally, IL33 mRNA significantly correlated with PD-1 mRNA (FIG. 14$e$), which has been associated with longer survival[22], suggesting the IL33-PD-1 axis may positively impact human PDAC survival. In summary, activating ILC2s with rIL33 can amplify responses to αPD-1 in both PD-1 partially sensitive and PD-1 resistant tumors.

Discussion

Our results suggest that activating ILC2s could be a broader strategy to enhance T cell priming in ILC2-infiltrated cancers (FIG. 14$f$). However, given the tissue-specific phenotypes of ILC2s, whether activating them will have similar effects across diverse cancers requires further study.

ILC2s can express immune checkpoints, yet their ability to be harnessed by immune checkpoint blockade therapy has remained unclear. We identify that blocking PD-1 on activated ILC2s has anti-tumor effects, suggesting ILC2s may partially contribute to the efficacy of PD-1 pathway blockade in human cancers, and highlighting more broadly that differential checkpoint blockade responses may be dependent on tissue-specific factors.

The expression of several immune modulatory molecules by activated ILC2s (FIG. 14$g$) suggests a broader array of checkpoints can be targeted on ILC2s and T cells in tumors. As ILC2 and T cells co-exist in human cancers with shared costimulatory and coinhibitory pathways, strategies to collectively target ILC2s and T cells for cancer immunotherapy are warranted.

The data presented in this Example was published by the inventors in the journal Nature (see, Moral et al., "ILC2s amplify PD-1 blockade by activating tissue-specific cancer immunity," Nature, 2020 March, Vol. 579 (7797), pp 130-135.doi: 10.1038/s41586-020-2015-4, Epub 2020 Feb. 19. The entire contents of this publication, including supplemental materials, is incorporated herein by reference.

Example 2

Materials & Methods

This Example described the materials & methods used in carrying the experiments described in Example 1

Mice

C57BL/6 (wild type, WT, CD45.2), C57BL/6 CD45.1, Rag2$^{-/-}$, Rag2$^{-/-}$ γc$^{-/-}$, Batf3$^{-/-}$, and Pdcd1$^{-/-}$ mice were purchased from Jackson Labs. Il33$^{-/-}$, Il33$^{Cit/+}$ were a gift from M. J. Rosen. Cd4$^{Cre/+}$Icos$^{fl-Dtr/+}$ and Il7r$^{Cre/+}$Rorα$^{fl/fl}$ were a gift from A. N. J. Mckenzie and have been previously described[16,23]. For all experiments, 6-12-week old mice were matched by age and sex and randomly assigned to specific treatment groups, with at least two independent experiments performed throughout. Pdx1-Cre; LSL-Kras$^{G12D/+}$; LSL-Trp53$^{R172H/+}$ (KPC mice) have been previously described[4]. Sample sizes for experiments were determined without formal power calculations. Animals were bred and maintained in a specific pathogen-free animal facility, and all experiments were conducted in accordance with an Institutional Animal Care and Use Committee (IACUC) approved protocol at Memorial Sloan Kettering Cancer Center (MSKCC) and in compliance with all relevant ethical regulations.

Cell Lines and Animal Procedures

All tumor cell lines were derived from KPC mice. KPC 4662 cells from Pdx1-Cre; LSL-Kras$^{G12D/+}$; LSL-Trp53$^{R172H/+}$ (a gift of R. H. Vonderheide) were transfected with GFP and used for all experiments unless indicated otherwise. KPC 8-1, 18-3, and 52 cells derived from Ptf1a-Cre; LSL-Kras$^{G12D/+}$; LSL-Trp53$^{R172H/+}$ mice were a gift of C. Iacobuzio-Donahue. KPC 4662 cells engineered to express OVA were previously described[24] (a gift of R. H. Vonderheide). All cell lines were authenticated as bonafide PDAC cell lines based on histopathologic verification by a dedicated pancreatic cancer pathologist. Orthotopic tumors established with KPC 4662 cells were IL33$^{High}$ and transiently decreased in size with αPD-1 therapy initiated at time of implantation (αPD-1 partial sensitivity). Orthotopic tumors established with KPC 52 cells were IL33$^{Low}$ and did not decrease in size with αPD-1 therapy initiated at time of implantation (αPD-1 resistant). All cell lines were regularly tested using MycoAlert Mycoplasma Detection Kit (Lonza). Orthotopic PDAC tumors were established as previously described[5]. Briefly, mice were anesthetized using a ketamine/xylazine cocktail and a small (7 mm) left abdominal side incision was made. Tumor cells (10$^6$ KPC cells/mouse; 1.25×10$^5$ KPC-OVA cells/mouse) were suspended in Matrigel (Becton Dickinson), diluted 1:1 with cold phosphate-buffered saline (PBS) (total volume of 50 μl), and injected into the tail of the pancreas using a 26-gauge needle. Successful injection was verified by the appearance of a fluid bubble without intraperitoneal leakage. The abdominal wall was closed with absorbable Vicryl RAPIDE sutures (Ethicon), and the skin was closed with wound clips (Roboz). For subcutaneous PDAC tumors, tumor cells (10$^6$ KPC cells/mouse; 1.25×10$^5$ KPC-OVA cells/mouse) were resuspended in sterile PBS (Fisher Scientific) and implanted subcutaneously. Mice were sacrificed at the indicated time points and processed for histology or flow cytometry. Autochthonous KPC mice were sacrificed when tumors were detectable by ultrasound. Tumor volumes were measured using serial ultrasound (Vevo 2100 Linear Array Imaging and Vivo LAB Version 3.1.1, Fuji Film Visual Sonics) for orthotopic tumors as previously described[25]. For subcutaneous tumors, tumor length and width were measured every 2-3 days by calipers, and tumor volumes were calculated as Volume=1/2 Length×Width². For survival analyses, survival was determined by a tumor volume of ≥500 mm³ or mouse health requiring euthanasia as defined by institutional IACUC guidelines. No mouse tumors exceeded IACUC-defined maximal tumor volumes of ≥2 cm³. No blinding was performed in experimental mouse interventions, as knowledge of the treatment groups was required.

T Cell Depletion CD4 and CD8 cells were depleted by intraperitoneal (i.p.) injection of 250 μg of anti-mouse CD4 antibody (clone GK1.5, BioXcell, In VivoPlus) and 250 μg of anti-mouse CD8a antibody (clone 2.43, BioXcell, In VivoPlus). Control mice were treated with rat IgG2b isotype control (clone LTF-2, BioXcell, InVivoPlus). Mice were treated daily for 3 days prior to tumor implantation, and then every 3 days for the duration of the experiment. CD4⁺ and CD8⁺ T cell depletion were confirmed by flow cytometric analysis of tumors and secondary lymphoid organs (>85% depletion).

ILC Depletion

ILCs were depleted in Rag2⁻/⁻ mice by i.p. injection of 300 μg of anti-mouse CD90.2 (clone 30-H12, BioXCell) on day 0, 1, 3, 6, 9, and 13 following tumor implantation as previously described[26]. ILC2s were depleted in Cd4$^{Cre/+}$ Icos$^{fl\text{-}DTR/+}$ experimental mice and Cd4$^{Cre/+}$ Icos$^{+/+}$ control mice treated by i.p. injection of diphtheria toxin (Sigma Aldrich) at a dosage of 25 ng per gram of mouse body weight. Mice were treated the day before tumor implantation and then every other day thereafter for a total of 5 doses as previously described[16]. ILC2 depletion was confirmed by flow cytometric analysis of tumors (FIG. 9a).

Bone Marrow Chimeras

Bone marrow was harvested from CD45.2 congenically labeled donor mice, filtered through a 70-mm filter, centrifuged, and resuspended in sterile PBS to a concentration of 10⁸ live cells per 200 μl. CD45.1 congenically labeled C57BL/6J recipient mice were irradiated (5.5 Gy×2, 6 hours apart) 24 hours before bone marrow transplant and were maintained on endofloxacin water for 4 weeks post irradiation. A single-cell suspension of CD45.2 bone marrow chimera in sterile PBS (10⁸ live cells per recipient mouse) was transplanted to each recipient mouse by retroorbital injection. Reconstitution was confirmed by flow cytometry of the peripheral blood at 4 and 8 weeks post transplantation. Tumor implantation experiments were performed at 12 weeks post transplantation.

Recombinant IL33, IL18, and PD-1 Blockade

For rIL33, mice were treated with intraperitoneal (i.p.) injections of 500 ng of carrier-free recombinant murine IL33 (R&D Systems) in sterile PBS daily for 7 days, and then every 2 days thereafter as previously described[15]. For rIL18, mice were treated with i.p. injection of 2 μg of carrier-free recombinant murine IL-18 (R&D Systems) in sterile PBS at days 3, 7, 11, and 15 after tumor inoculation as previously described[27]. The chimeric anti-mouse PD-1 antibody (4H2) used in this study engineered as a mouse IgG1 isotype monoclonal antibody (mAb) was shown to bind to CHO transfectants expressing PD-1 and block binding of PD-L1 and PD-L2 to these cells. The affinity of 4H2 for mouse PD-1, determined by surface plasmon resonance using PD-1-Fc, was 4.68×10⁻⁹ M. The antibody was produced and purified at Bristol Myers Squibb (BMS). Each batch was certified to have <0.5 EU/mg endotoxin and be of >95% purity. All dosing solutions were prepared in PBS. Mice were treated with i.p. injection of 250 μg anti-PD1 every 2 days. Transient reduction in tumor size but subsequent regrowth while on continuous αPD-1 treatment was defined as a partial response. No reduction in tumor size while on continuous αPD-1 was defined as resistance.

Human Samples

All tissues were collected at MSKCC following study protocol approval by the MSKCC Institutional Review Board. Informed consent was obtained for all patients. The study was performed in strict compliance with all institutional ethical regulations. All tumor samples were surgically resected primary PDACs.

Tissue microarray: Tissue microarrays (TMAs) were constructed from tumor and adjacent non-tumor cores from formalin-fixed, paraffin-embedded tissue blocks from short-term survivors (n=45 tumors, 5 normal tissue) and long-term survivors (n=51 tumors, 5 normal tissue) of PDAC as previously described[3]. Patient subsets were randomly selected to undergo tissue microarray construction. Patients treated with neoadjuvant therapy were excluded. All tumors were subjected to pathological re-review and histological confirmation by two expert PDAC pathologists before analysis. Long-term survivors were defined as patients with overall survival of >3 years from surgery and short-term survivors as patients with survival >3 months and <1 year from surgery, to exclude perioperative mortalities. ILC2$^{High}$ and ILC2$^{Low}$ were defined as greater or lesser, respectively, than the median ILC2 frequency for the entire TMA cohort.

Tumor transcriptomic profiling: Patient subsets were randomly selected to undergo transcriptomic profiling as previously described[3]. Patients in the TMA cohort with tumor tissue available for transcriptomic assessment were included in analyses in FIG. 1b to allow protein confirmation of RNA expression. Extracted RNA was qualified on an Agilent BioAnalyzer and quantified by fluorometry (Ribogreen). Preparation of RNA for whole-transcriptome expression analysis was done using the WT Pico Reagent Kit (Affymetrix). Reverse transcription was initiated at the poly-A tail as well as throughout the entire length of RNA to capture both coding and multiple forms of non-coding RNA. RNA amplification was achieved using low-cycle PCR followed by linear amplification using T7 in vitro transcription technology. The cRNA was then converted to biotinylated sense-strand DNA hybridization targets. The prepared target was hybridized to GeneChip Human Transcriptome Array 2.0 (Affymetrix). Washes were performed using the GeneChip Hybridization, Wash and Stain Kit using a Fluidics Station 450/250. Arrays were scanned using the GeneChip Scanner 3000. Data analysis for the array was done using Affymetrix Expression Console Software (SST-RMA algorithm to summarize the signal from array probesets). Immune cytolytic activity was determined as previously described[28].

Cell Isolation

Mouse and human PDAC tumors and adjacent pancreata were mechanically dissociated and incubated in collagenase (collagenase II for murine tumors, collagenase IV for human tumors, both 5 mg/ml; Worthington Biochemical Corp., Fisher Scientific), DNAse I (0.5 mg/ml; Roche Diagnostics), and Hank's balanced salt solution (Gibco, Fisher Scientific) for 30 minutes at 37° C. Digestion was then quenched with fetal bovine serum (FBS, Life Technologies), and cells were filtered sequentially through 100- and 40-mm nylon cell strainers (Falcon, Fisher Scientific). Tumors, adjacent pancreata, and lymph nodes were then mechanically disassociated and filtered through 100- and 40-mm nylon cell strainers (Falcon, Fisher Scientific) using PBS with 1% FBS (Life Technologies). Spleens were mechanically dissociated and filtered through 70- and 40-mm nylon cell strainers (Falcon, Fisher Scientific) using PBS with 1% FBS, followed by RBC lysis (RBC lysis buffer, ThermoFisher Scientific). Mouse Fc receptors were blocked with FcεRIII/II-specific antibody (1 μg per $1 \times 10^6$ cells; clone 2.4G2, Bio X Cell).

ILC2 Adoptive Transfer

CD45.1 C57Bl/6 or $Pdcd1^{-/-}$ orthotopic PDAC mice were treated with 500 ng of carrier-free recombinant murine IL33 (R&D Systems) in sterile PBS daily for 10 days. Live, $CD45^+$, lineage, $CD90^+$, $CD25^+$, $ST2^+$ TILC2s were sort-purified to 98% purity at day 10 post-implantation using an Aria Cell sorter (BD Biosciences). $5 \times 10^5$ tumor ILC2s were immediately transferred to orthotopic PDAC tumor-bearing $Il7r^{Cre/+}$ $Ror\alpha^{fl/fl}$ CD45.2 mice days 7 and 14 post-tumor implantation via i.p. injection. Control mice received equivalent volumes of PBS via i.p. injection. αPD-1 treatment in recipient mice was initiated on the day of ILC2 cell transfer. Tissues were harvested at indicated time points.

Flow Cytometry

Single-cell suspensions were stained using antibody cocktails in the dark at 4° C., washed, and analyzed on a FACS LSR Fortessa (BD Biosciences). Mouse ILCs were defined as live, $CD45^+$, lineage (CD3, CD5, NK1.1, CD11b, CD11c, CD19, FcεR1), $CD25^+$, $CD127^+$ cells as previously described[7, 1]. Mouse immune cells were defined as follows: ILC2s=live, $CD45^+$, lineage $CD25^+$, $ST2^+$ cells; central memory T cells=live, $CD45^+$, $CD3^+$, NK1.1, $CD8^+$, $CD62l^+$, $CD44^+$; dendritic cells=live, $CD45^+$, $CD3^-$, NK1.1, Gr1, $F4/80^-$, $CD11c^+$, MHC-II$^+$; B cells=live, $CD45^+$, $CD3^-$, $CD19^+$; T cells=live, $CD45^+$, $CD3^+$; $CD4^+$ T cells=live, $CD45^+$, $CD3^+$, $CD4^+$; $CD8^+$ T cells=live, $CD45^+$, $CD3^+$, $CD8^+$; regulatory T cells=live, $CD45^+$, $CD3^+$, $CD4^+$ $FoxP3^+$; tumor associated macrophages=live, $CD45^+$, $CD11b^+$, $F4\backslash80^+$, GR1; myeloid derived suppressor cells (MDSCs)=live, $CD45^+$, $CD3^-$, $CD11b^+$, $F4\backslash80^-$, $GR1^+$. Murine cells were stained with the following antibodies: from Biolegend, CD45 (clone 30-F11, Pacific Blue), CD45.1 (clone A20, BV711), NK1.1 (clone PK136, APC), Gr-1 (clone RB6-8C5, BV605), CD103 (clone 2E7, BV711); from BD Biosciences, CD5 (clone 53-7.3, APC), CD11c (clone HL3, APC), NK1.1 (clone PK136, BV605), CD4 (clone RM4-5, BV786), CD62L (clone MEL-14, APC), CD19 (clone 1D3, BV510), Ly6C (clone AL-21, PerCP-Cy5.5), Ly6G (clone 1A8, AF700), PD1 (clone J43 BV605), TNF-α (clone MP6-XT22, BV510), IFN-γ (clone XMG1.2, APC-Cy7), CD90.2 (clone 53-2.1, BV786), Tbet (clone Q4-46, BV711), Rorγ-t (clone Q31-378, BV786), Gata3 (clone L50-823, PE-Cy7), and IL4 (clone 11B11, BV650); from ThermoFisher Scientific CD3 (clone 17A2, Alexa Fluor 700), CD11b (clone M1/70, APC), CD11b (clone M1/70, PerCP-Cy5.5), CD8 (clone 53-6.7, Alexa Fluor 700), CD19 (clone 1D3, Alexa Fluor 700), FcεR1 (clone MAR-1, APC), F4/80 (clone BM8, PE-Cy5), CD3 (clone 145-2C11, PE-Cy7), MHC-II (clone M5/114.15.2, Alexa Fluor 700), CD44 (clone IM7, PerCP-Cy5.5), CD127 (clone A7R34, FITC), CD25 (clone PC61.5, PerCP-Cy5.5), IL5 (clone TRFK5, PE), CD86 (clone GL1, PE), CD11c (clone N418, FITC), ST2 (clone RMST2-2, PE-Cy7), and FoxP3 (clone FJK-16S, APC); and from MBL international, SINFEKL tetramer (catalog #TB-5001-1, PE).

Human ILCs were defined as live $CD45^+$, lineage (CD3, CD5, CD56, CD11b, CD11c, CD16, CD19, TCRα/β, FcεR1), $CD25^+$, $CD127^+$ cells as previously described[7]. Human cells were stained with the following antibodies: from BD Biosciences, GATA3 (clone L50-823, BV711), TBET (clone O4-46, BV650), RORγ-T (clone Q21-559, PE); from Biolegend, CRTH2 (clone BM16, PE-Cy7), CD11b (clone ICRF44, APC), CD56 (clone NCAM16.2, BV650), CD25 (clone BC96, PerCP-Cy5.5), CD45 (clone HI30, Pacific Blue), TCRα/β (clone IP26, APC); from ThermoFisher Scientific, CD16 (clone CB16, APC), CD11c (clone 3.9, APC), CD127 (clone RDR5, FITC), CD3 (clone OKT3, Alexa Fluor 700), ST2 (clone hIL33Rcap, PE), CD5 (clone L17F12, APC), CD19 (clone HIB19, AF700), FcεR1 (clone AER-37, APC). Human-specific antibody to IL33 (clone 390412, PE) was purchased from R&D Systems. All samples for flow cytometry were from prospectively collected unselected PDAC patients.

To examine intracellular cytokine production, singe-cell suspensions of tumors were stimulated for 6 hours ex-vivo with phorbol 12-myristate (PMA, 100 ng/ml) and ionomycin (1 ng/ml) in the presence of brefeldin A (10 μg/ml) (all from Sigma-Aldrich) at 37° C. Cells were then surface-stained, fixed, permeabilized, and stained for cytokine production using the Fixation and Permeabilization Buffer Kit per the manufacturer's recommendations (Invitrogen, ThermoFisher Scientific). Appropriate isotype controls were used as indicated. Analysis was performed on FlowJo (versions 9 and 10, Tree Star).

Immunohistochemistry

Tissues were fixed in paraformaldehyde (Fisher Scientific) for 24 hours and embedded in paraffin. The tissue sections were deparaffinized with EZPrep buffer (Ventana Medical Systems), then antigen retrieval was performed with CCI buffer (Ventana Medical Systems). Sections were blocked for 30 minutes with Background Buster solution (Innovex), followed by avidin-biotin blocking for 8 minutes (Ventana Medical Systems). Mouse IL33 (AF3626, R&D Systems), mouse smooth muscle actin (Abcam), and human IL33 (AF3625, R&D Systems) antibodies were applied, and sections were incubated for 4 hours, followed by a 60-minute incubation with biotinylated rabbit anti-goat IgG (Vector labs), or biotinylated goat anti-rabbit IgG (Vector labs) at 1:200 dilution. Detection was performed with DAB detection kit (Ventana Medical Systems) according to the manufacturer's instructions. Any section containing cells demonstrating cytoplasmic or nuclear positivity for IL33 was designated to have positive staining. Slides were counter-stained with Masson's trichrome, or hematoxylin, and eosin, and cover-slipped with Permount (Fisher Scientific). All histologic sections were evaluated by an independent PDAC pathologist.

Immunofluorescence

Mouse

IL33/CD11b/CK19/Iba1 immunofluorescence: Multiplex immunofluorescent staining was performed using a Discovery XT processor (Ventana Medical Systems) as described[29].

IL33: First, sections were incubated with anti-mIL33 (R&D Systems, catalog #AF3626, 1 μg/ml) for 4 hours, followed by 60 minutes incubation with biotinylated horse anti-goat IgG (Vector Laboratories) at 1:200 dilution. Detection was performed with Streptavidin-HRP D (part of DAB-Map kit, Ventana Medical Systems), followed by incubation with Tyramide Alexa Fluor 488 (Invitrogen) prepared according to the manufacturer's instructions with predetermined dilutions.

CD11b: Next, sections were incubated with anti-CD11b (Abcam, clone EPR1544) for 5 hours, followed by 60 minutes incubation with biotinylated goat anti-rabbit IgG (Vector Laboratories) at 1:200 dilution. Detection was performed with Streptavidin-HRP D (part of DABMap kit, Ventana Medical Systems), followed by incubation with Tyramide Alexa 594 (Invitrogen) prepared according to the manufacturer's instructions with predetermined dilutions.

CK19: Next, slides were incubated with anti-CK19 (Abcam, clone EP1580Y) for 5 hours, followed by 60 minutes incubation with biotinylated goat anti-rabbit (Vector Laboratories) at 1:200 dilution. Detection was performed with Streptavidin-HRP D (part of DABMap kit, Ventana Medical Systems), followed by incubation with Tyramide Alexa Fluor 546 (Invitrogen) prepared according to the manufacturer's instructions with predetermined dilutions Iba1: Finally, sections were incubated with anti-Iba1 (Wako, catalog #019-19741) for 5 hours, followed by 60 minutes incubation with biotinylated goat anti-rabbit IgG (Vector Laboratories) at 1:200 dilution. Detection was performed with Streptavidin-HRP D (part of DABMap kit, Ventana Medical Systems), followed by incubation with Tyramide Alexa 647 (Invitrogen) prepared according to the manufacturer's instructions with predetermined dilutions. After staining, slides were counterstained with DAPI (Sigma Aldrich) for 10 min and cover-slipped with Mowiol.

Human

The tissue sections were deparaffinized with proprietary Leica Bond buffer (Leica Biosystems), antigen retrieval was performed with Leica Bond ER2 buffer (Leica Biosystems). First, sections were incubated with anti-PD-1 antibodies (Cell Marque, clone NAT105) for 1 hour, followed by detection with Bond Polymer Refine Detection kit (Leica Biosystems) and Tyramide Alexa Fluor 488 (Invitrogen). Next, sections were incubated with anti-CD3 antibodies (DAKO, catalog #A0452) for 1 hour, followed by detection with Bond Polymer Refine Detection kit (Leica Biosystems) and Tyramide CF594 (Biotum). Next, sections were incubated with anti-GATA3 antibodies (Cell Marque, clone L50-823) for 1 hour, followed by detection with Bond Polymer Refine Detection kit (Leica Biosystems) and CF 543 (Biotum). Finally, sections were incubated with anti-CD45 antibodies (DAKO, clone 2B11+PD7/26) for 1 hour, followed by detection with Bond Polymer Refine Detection kit (Leica Biosystems) and Tyramide Alexa Fluor 647 (Invitrogen). All detections were prepared according to manufacturer instruction with predetermined dilutions. After staining, slides were counterstained with DAPI (Sigma Aldrich) for 10 min and cover-slipped with Mowiol.

Digital Image Processing and Analysis

The slides were digitized using Panoramic Flash 250 (3Dhistech, Budapest Hungary) using Zeiss 20×/0.8NA objective and custom filters for A488, A546, A594, and A647. Each core was exported into multi-channel tiff files and analyzed using custom macro written in FIJI/ImageJ. For quantification, each nucleus was segmented using the DAPI channel after appropriate processing and background subtraction. Then for each nucleated cell, the presence or absence of the other markers were assessed after setting appropriate thresholds for each marker. The number of cells with specific combinations of markers were tallied. ILC2s were defined as $CD45^+$ $CD3^-$ $GATA3^+$ nucleated cells, PD-1 expressing ILC2s were defined as $CD45^+$ $CD3^-$ $GATA3^+$ $PD-1^+$ nucleated cells, and PD-1 expressing T cells were defined as $CD45^+$ $CD3^+$ $PD-1^+$ nucleated cells. For each patient, the frequency of each cell type as a fraction of all nucleated cells was calculated in triplicate cores, followed by determination of the mean frequency of triplicate cores to calculate the final cellular frequency per patient.

RNA Sequencing

Mouse: Tissues from orthotopic PDAC mice (n=6) were harvested and dissociated into single-cell suspensions as described above. Tumor-infiltrating leukocytes were positively selected by magnetically activated cell sorting using mouse CD45 MicroBeads (Miltenyi Biotec). Purification of magnetically activated sorted cells was confirmed by flow cytometry and was >95%. RNA was isolated from the sorted cells using an RNeasy Plus Mini Kit (Qiagen). Poly(A) capture and paired-end RNA-seq were performed by the MSKCC Integrated Genomics Core Facility. Specifically, after RiboGreen quantification and quality control by Agilent BioAnalyzer, 500 ng of total RNA underwent polyA selection and TruSeq library preparation according to instructions provided by Illumina (TruSeq Stranded mRNA LT Kit, catalog #RS-122-2102), with 8 cycles of PCR. Samples were barcoded and ran on a HiSeq 4000 in a 100 bp/100 bp paired-end run, using the HiSeq 3000/4000 SBS Kit (Illumina). An average of 83 million paired reads was generated per sample. Ribosomal reads represented at most 0.03% of the total reads generated, and the percentage of mRNA bases averaged 76.6%. The expression dataset was loaded into Gene Set Enrichment Analysis (GSEA) 3.0. Gene set databases for antigen presentation and T cell mediated immunity were selected from MSIGDB v6.1, with a false discovery rate of ≤0.25 to facilitate exploratory discovery. GSEA was run with 1000 permutations. Three gene set databases met this threshold: GO 0002474 Antigen Processing and Presentation of Peptide Antigen Via MHC Class I, GO 0002711 Positive Regulation of T Cell Mediated Immunity, and GSE19825 Naïve vs Day 3 Effector CD8 T Cell Up.

Single-Cell RNA Sequencing

Library preparation for single-cell immune profiling, sequencing, and post-processing of the raw data was performed at the Epigenomics Core at Weill Cornell Medicine.

Single-Cell RNA Library Preparation and Sequencing

Single-cell suspensions of fluorescence activated cell (FAC)-sorted ILC2 cells from vehicle, IL33 alone, and IL33+αPD-1 treated pancreatic KPC tumors and mesenteric DLNs were prepared as described above. scRNA-seq libraries were prepared according to 10× Genomics specifications (Chromium Single Cell V (D) J User Guide PN-1000006, 10× Genomics, Pleasanton, CA, USA). Four independent cellular suspensions (85-90% viable) at a concentration between 90-200 cells/µl, were loaded onto to the 10× Genomics Chromium platform to generate Gel Beads-in-Emulsion (GEM), targeting about 2,000 single cells per sample. After GEM generation, the samples were subjected to an incubation at 53° C. for 45 min in a C1000 Touch Thermal cycler with 96-Deep Well Reaction Module (Bio-Rad, Hercules) to generate poly A cDNA barcoded at the 5' end by the addition of a template switch oligo (TSO) linked to a cell barcode and Unique Molecular Identifiers (UMIs). GEMs were broken, and the single-strand cDNA was cleaned up with DynaBeads MyOne Silane Beads (Thermo Fisher Scientific, Waltham, MA). The cDNA was amplified for 16 cycles (98° C. for 45 s; 98° C. for 20 s, 67° C. for 30 s, 72° C. for 1 hr). Quality of the cDNA was assessed using an Agilent Bioanalyzer 2100 (Santa Clara, CA), obtaining a product of about 1,200 bp. 50 ng of cDNA was enzymatically fragmented, end repaired, A-tailed, subjected to a double-sided size selection with SPRIselect beads (Beckman Coulter, Indianapolis, IN), and ligated to adaptors provided in the kit. A unique sample index for each library was introduced through 14 cycles of PCR amplification using the indexes provided in the kit (98° C. for 45 s; 98° C. for 20 s, 54° C. for 30 s, and 72° C. for 20 s×14 cycles; 72° C. for 1 min; held at 4° C.). Indexed libraries were subjected to a second double-sided size selection, and libraries were then quantified using Qubit fluorometric quantification (Thermo Fisher Scientific, Waltham, MA). The quality was assessed on an Agilent Bioanalyzer 2100, obtaining an average library size of 450 bp. No treatment samples had concentrations below detectable limits, and cDNA amplification was done with 18 cycles and sample Index with 16 cycles. Libraries were diluted to 10 nM and clustered using a NovaSeq600 on a pair end read flow cell and sequenced for 28 cycles on R1 (10× barcode and the UMIs), followed by 8 cycles of 17 Index (sample Index), and 89 bases on R2 (transcript), obtaining about 100 million clusters per sample, except for tumors from vehicle-treated mice which was clustered at about 10 million. Primary processing of sequencing images was done using Illumina's Real Time Analysis software (RTA). 10× Genomics Cell Ranger Single Cell Software suite v3.0.2 (available at web site "support. 10×genomics.com" under "single-cell-gene-expression/ software/pipelines/latest/what-is-cell-ranger") was used to perform sample demultiplexing, alignment to mouse genomic reference mm 10, filtering, UMI counting, single-cell 5' end gene counting, and quality control using the manufacturer parameters. Data from approximately 11,000 single cells that passed quality control were obtained with approximately 41,000 mean reads per cell (48% sequencing saturation).

scRNA-Seg Data Processing

The Seurat R package version 3.1 pipeline was used to identify clusters on combined datasets[30]. First, individual datasets were read into R as count matrices and converted into Seurat objects, selecting on genes expressed in ≥3 cells and on cells with at least 200 detected genes. A standard pre-processing workflow was then used to filter cells based on excluding cells with either over 2,500 or less than 200 unique genes expressed, and cells with greater than 5% mitochondrial gene content.

Following filtering, the samples were merged, and the gene expression measurements for retained cells were log-transformed, normalized by total expression per cell, and scaled to 10,000 molecules per cell. The top 2,000 highly variable genes across the single cells were then identified, and principal components (PCs) analysis was conducted. After examining jackstraw and elbow plots, we selected the top 15 PCs for clustering using K-nearest neighbor (KNN) clustering with cluster resolution set at 0.4, identifying 6-8 clusters in all samples-combined and tumor-combined merged datasets. Non-linear dimensional reduction with UMAP was used to visualize the datasets also using the top 15 PCs. Differential gene expression for gene marker discovery across the clusters was performed using the Wilcoxon rank sum test as used in the Seurat package. Pairwise comparison using Wilcoxon rank sum test was performed with holm P value adjustment method to compare gene expression between samples.

In Vitro Assays

KPC 4662-GFP cells were cultured for 1 week in a 96-well flat-bottomed plate (Falcon) in complete media: RPMI-1640 with L-glutamine (Gibco, ThermoFisher) with 10% fetal bovine serum (Life Technologies), 100 units/ml of penicillin, 100 µg/ml of streptomycin, and recombinant IL33 at concentrations of 0, 10, 100, and 500 ng/ml. Culture media and cytokines were replenished every 48 hours. Viability was measured using a colorimetric tetrazolium salt assay (Cell Counting Kit, Dojindo Molecular Technologies) per the manufacturer's instructions and read on a Synergy HT Multi-Detection Microplate Reader (Biotek). Cells were harvested and stained for Annexin V (ThermoFisher Scientific), Ki-67 (clone SolA15, ThermoFisher Scientific), and ST2 (clone RMST2, ThermoFisher Scientific). For all in vitro experiments, 2-3 technical replicates were performed per independent experiment.

In Vitro Dendritic Cell Migration Assays

Murine splenic DC were isolated and enriched using a mouse pan DC isolation kit according to the manufacturer's protocol (Miltenyi Biotech). Flow cytometry was used to assess DC purity (>70% CD11c⁺ of live cells). Cells were plated in complete RPMI media at $5 \times 10^5$ cells/ml with 50 ng/ml of recombinant mouse GM-CSF (Biolegend) overnight. Next, chemotaxis of splenic DCs was analyzed by transwell migration assays. 600 µl of RPMI with or without 100 ng/ml of recombinant mouse Ccl5 (Biolegend) was added to the lower chambers of a 6.5-mm Transwell plate with 5.0-µm pore polycarbonate membrane inserts (Sigma Aldrich). 200 µl of RPMI was also added to the upper chambers and plates were allowed to equilibrate at 37° C. in 5% $CO_2$ for 15 minutes. $1 \times 10^5$ splenic DCs in 100 µl of RPMI were then loaded into the upper chambers, and incubated at 37° C. in 5% $CO_2$ for 2 hours. After incubation, membrane inserts were carefully removed, and cells were harvested from the lower chambers. Migrated DCs were incubated with DAPI and CD11c antibodies for 20 minutes at 4° C., and Precision Count Beads™ (Biolegend) were added to quantify the number of live, migrated, CD11c⁺ cells using flow cytometry according to manufacturer's protocol.

Statistics

Data are expressed as median. As we observed many statistically significant effects in the data without a priori sample size calculations, no statistical methods were used to determine sample size. Comparisons between two groups were performed using unpaired Mann-Whitney test with the Benjamini-Krieger-Yekutieli false discovery approach for multiple time point comparisons (2-tailed). Comparisons among multiple groups were performed using 1-way ANOVA test followed by Kruskal Wallis multiple comparison post-test. Comparisons among multiple groups across multiple time points were performed using 2-way ANOVA test. Correlations between 2 variables were calculated using linear regression. Survival curves were compared by 2-sided log-rank test. Tumor incidences were compared by Chi-square test. All alpha levels were 0.05, with P<0.05 considered a significant difference. Statistical analyses were performed using Prism 7.0 (GraphPad Software).

The information presented in this Example was published by the inventors in the journal Nature (see, Moral et al., "ILC2s amplify PD-1 blockade by activating tissue-specific cancer immunity," Nature, 2020 March, Vol. 579 (7797), pp 130-135.doi: 10.1038/s41586-020-2015-4, Epub 2020 Feb. 19. The entire contents of this publication, including supplemental materials, is incorporated herein by reference.

Example 3

Effective Treatment of PDAC in Mice Using IL33-Activated ILC2 Cell Therapy

Experiments were performed to assess the efficacy of IL33-activated ILC2 cell therapy using a mouse model of PDAC. Unless otherwise stated, the mice, PDAC models, active agents (IL33, αPD-1), and protocols were as described above in Examples 1 & 2. IL33 was administered to "donor" mice to activate pancreatic tumor ILC2 cells. Pancreatic tumor ILC2 cells were then isolated from the donor mice, purified, and administered to "recipient" ILC2-deficient mice having established PDAC tumors. Anti-PD-1 antibody was also administered to some of the recipient mice. In the recipient mice that received the donor ILC2 cells alone there was no significant effect on the PDAC tumors, but in the recipient mice that received the donor ILC2 cells and the anti-PD-1 antibody there was a significant reduction in size of the PDAC tumors.

Example 4

Human Clinical Trial

Clinical trials are performed to demonstrate the safety and/or efficacy of treatment of PDAC Clinical trials are performed to demonstrate the safety and/or efficacy of treatment of PDAC using IL33 and/or PD-1/PD-L1 inhibitors in adult human subjects. Patients with PDAC are identified and enrolled. Patients are assigned to a particular groups. The different groups receive either: (a) IL33 alone, (b) an approved PD-1 and/or PD-L1 inhibitor alone, or (c) IL33 and an approved PD-1 and/or PD-L1 inhibitor. Within each group, there can be multiple different sub-groups in which different agents (e.g. different PD-1/PD-L1 inhibitors), different doses, different and different dosing schedules etc. are used. The IL33 is administered intravenously (IV). In some sub-groups the IL33 may be in its native form. In some sub-groups the IL33 may be modified by inclusion of one or more half-life improving moieties. Different sub-groups may receive different doses of IL33 (within a range possible doses). Different sub-groups may receive the IL33 at different frequencies (e.g. daily, or every 2, 3, 4, 5, 6, or 7 days). The approved PD-1 and/or PD-L1 inhibitor is administered at an approved dose, by an approved dosing schedule, and by an approved administration route (e.g. based on such criteria as approved for the treatment of any cancer).

REFERENCES

1. Vivier, E. et al. Innate Lymphoid Cells: 10 Years On. *Cell* 174, 1054-1066 (2018).
2 Salimi, M. et al. Activated innate lymphoid cell populations accumulate in human tumour tissues. *BMC Cancer* 18, 341 (2018).
3. Balachandran, V. P. et al. Identification of unique neoantigen qualities in long-term survivors of pancreatic cancer. *Nature* 551, 512-516 (2017).
4. Hingorani, S. R. et al. Trp53R172H and KrasG12D cooperate to promote chromosomal instability and widely metastatic pancreatic ductal adenocarcinoma in mice. *Cancer Cell* 7, 469-483 (2005).
5. Pylayeva-Gupta, Y., Lee, K. E., Hajdu, C. H., Miller, G. & Bar-Sagi, D. Oncogenic Kras-induced GM-CSF production promotes the development of pancreatic neoplasia. *Cancer Cell* 21, 836-847 (2012).
6 Li, J. et al. Tumor Cell-Intrinsic Factors Underlie Heterogeneity of Immune Cell Infiltration and Response to Immunotherapy. *Immunity* 49, 178-193.e7 (2018).
7. Brestoff, J. R. et al. Group 2 innate lymphoid cells promote beiging of white adipose tissue and limit obesity. *Nature* 519, 242-246 (2015).
8. Gasteiger, G., Fan, X., Dikiy, S., Lee, S. Y. & Rudensky, A. Y. Tissue residency of innate lymphoid cells in lymphoid and nonlymphoid organs. *Science* 350, 981-985 (2015).
9. Monticelli, L. A. et al. Arginase 1 is an innate lymphoid-cell-intrinsic metabolic checkpoint controlling type 2 inflammation. *Nat Immunol* 17, 656-665 (2016).
10. Kirchberger, S. et al. Innate lymphoid cells sustain colon cancer through production of interleukin-22 in a mouse model. *Journal of Experimental Medicine* 210, 917-931 (2013).
11. Neesse, A. et al. CTGF antagonism with mAb FG-3019 enhances chemotherapy response without increasing drug delivery in murine ductal pancreas cancer. *Proceedings of the National Academy of Sciences* 110, 12325-12330 (2013).
12. Hardman, C. S., Panova, V. & Mckenzie, A. N. J. IL-33 citrine reporter mice reveal the temporal and spatial expression of IL-33 during allergic lung inflammation. *Eur J Immunol* 43, 488-498 (2013).
13. Talabot-Ayer, D. et al. The mouse interleukin (II) 33 gene is expressed in a cell type- and stimulus-dependent manner from two alternative promoters. *J. Leukoc. Biol.* 91, 119-125 (2012).
14. Ricardo-Gonzalez, R. R. et al. Tissue signals imprint ILC2 identity with anticipatory function. *Nat Immunol* 19, 1093-1099 (2018).
15. Dalmas, E. et al. Interleukin-33-Activated Islet-Resident Innate Lymphoid Cells Promote Insulin Secretion through Myeloid Cell Retinoic Acid Production. *Immunity* 47, 928-942.e7 (2017).
16. Oliphant, C. J. et al. MHCII-mediated dialog between group 2 innate lymphoid cells and CD4(+) T cells potentiates type 2 immunity and promotes parasitic helminth expulsion. *Immunity* 41, 283-295 (2014).
17. Böttcher, J. P. et al. N K Cells Stimulate Recruitment of cDC1 into the Tumor Microenvironment Promoting Cancer Immune Control. *Cell* 172, 1022-1037.e14 (2018).
18. Miyamoto, C. et al. Runx/Cbfβ complexes protect group 2 innate lymphoid cells from exhausted-like hyporesponsiveness during allergic airway inflammation. *Nat Commun* 10, 447 (2019).
19. Yu, Y. et al. Single-cell RNA-seq identifies a PD-1hi ILC progenitor and defines its development pathway. *Nature* 539, 102-106 (2016).
20. Taylor, S. et al. PD-1 regulates KLRG1 (+) group 2 innate lymphoid cells. *Journal of Experimental Medicine* 214, 1663-1678 (2017).
21. Kim, J. et al. Intratumorally Establishing Type 2 Innate Lymphoid Cells Blocks Tumor Growth. *The Journal of Immunology* 196, 2410-2423 (2016).
22. Diana, A. et al. Prognostic value, localization and correlation of PD-1/PD-L1, CD8 and FOXP3 with the desmoplastic stroma in pancreatic ductal adenocarcinoma. *Oncotarget* 7, 40992-41004 (2016).
23. Donovan, C. et al. Roles for T/B lymphocytes and ILC2s in experimental chronic obstructive pulmonary disease. *J. Leukoc. Biol.* 105, 143-150 (2019).
24 Evans, R. A. et al. Lack of immunoediting in murine pancreatic cancer reversed with neoantigen. *JCI Insight* 1, (2016).
25. Sastra, S. A. & Olive, K. P. Quantification of murine pancreatic tumors by high-resolution ultrasound. *Methods Mol. Biol.* 980, 249-266 (2013).
26. Monticelli, L. A. et al. Innate lymphoid cells promote lung-tissue homeostasis after infection with influenza virus. *Nat Immunol* 12, 1045-1054 (2011).
27. Ma, Z. et al. Augmentation of Immune Checkpoint Cancer Immunotherapy with IL18. *Clin Cancer Res* 22, 2969-2980 (2016).
28. Rooney, M. S., Shukla, S. A., Wu, C. J., Getz, G. & Hacohen, N. Molecular and genetic properties of tumors associated with local immune cytolytic activity. *Cell* 160, 48-61 (2015).
29. Yarilin, D. et al. Machine-based method for multiplex in situ molecular characterization of tissues by immunofluorescence detection. *Sci Rep* 5, 9534 (2015).
30. Butler, A., Hoffman, P., Smibert, P., Papalexi, E. & Satija, R. Integrating single-cell transcriptomic data across different conditions, technologies, and species. *Nat Biotechnol* 36, 411-420 (2018).

We claim:

1. A method of treating pancreatic ductal adenocarcinoma (PDAC) in a subject in need thereof, the method comprising administering to a subject with PDAC an effective amount of IL33, thereby treating the PDAC in the subject.

2. The method of claim 1, further comprising administering to the subject an effective amount of a PD-1 and/or PD-L1 inhibitor.

3. The method of claim 2, wherein the PD-1 inhibitor is an antibody.

4. The method of claim 2, wherein the PD-1 inhibitor is selected from the group consisting of pembrolizumab, nivolumab, cemiplimab, AMP-224, AMP-514 and PDR001.

5. The method of claim 2, wherein the PD-L1 inhibitor is an antibody.

6. The method of claim 2, wherein the PD-L1 inhibitor is selected from the group consisting of atezolizumab, Avelumab, Durvalumab, BMS-936559 and CK-301.

7. The method of claim 1, wherein the subject has a PDAC that is partially or totally resistant to PD-1 and/or PD-L1 inhibitor treatment.

8. The method of claim 1, wherein the IL33 is recombinant IL33.

9. A pharmaceutical composition comprising: (a) IL33 and (b) a PD-1 and/or PD-L1 inhibitor.

* * * * *

SEQUENCE LISTING

<160> NUMBER OF SEQ ID NOS: 15

<210> SEQ ID NO 1
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ser Ile Thr Gly Ile Ser Pro Ile Thr Glu Tyr Leu Ala Ser Leu Ser
1               5                   10                  15

Thr Tyr Asn Asp Gln Ser Ile Thr Phe Ala Leu Glu Asp Glu Ser Tyr
            20                  25                  30

Glu Ile Tyr Val Glu Asp Leu Lys Lys Asp Glu Lys Lys Asp Lys Val
        35                  40                  45

Leu Leu Ser Tyr Tyr Glu Ser Gln His Pro Ser Asn Glu Ser Gly Asp
    50                  55                  60

Gly Val Asp Gly Lys Met Leu Met Val Thr Leu Ser Pro Thr Lys Asp
65                  70                  75                  80

Phe Trp Leu His Ala Asn Asn Lys Glu His Ser Val Glu Leu His Lys
                85                  90                  95

Cys Glu Lys Pro Leu Pro Asp Gln Ala Phe Phe Val Leu His Asn Met
                100                 105                 110

His Ser Asn Cys Val Ser Phe Glu Cys Lys Thr Asp Pro Gly Val Phe
        115                 120                 125

Ile Gly Val Lys Asp Asn His Leu Ala Leu Ile Lys Val Asp Ser Ser
    130                 135                 140

Glu Asn Leu Cys Thr Glu Asn Ile Leu Phe Lys Leu Ser Glu Thr
145                 150                 155

<210> SEQ ID NO 2
<211> LENGTH: 160
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ser Ser Ile Thr Gly Ile Ser Pro Ile Thr Glu Tyr Leu Ala Ser Leu
1               5                   10                  15

Ser Thr Tyr Asn Asp Gln Ser Ile Thr Phe Ala Leu Glu Asp Glu Ser
            20                  25                  30

Tyr Glu Ile Tyr Val Glu Asp Leu Lys Lys Asp Glu Lys Lys Asp Lys
        35                  40                  45

Val Leu Leu Ser Tyr Tyr Glu Ser Gln His Pro Ser Asn Glu Ser Gly
    50                  55                  60

Asp Gly Val Asp Gly Lys Met Leu Met Val Thr Leu Ser Pro Thr Lys
65                  70                  75                  80

Asp Phe Trp Leu His Ala Asn Asn Lys Glu His Ser Val Glu Leu His
                85                  90                  95

Lys Cys Glu Lys Pro Leu Pro Asp Gln Ala Phe Phe Val Leu His Asn
                100                 105                 110

Met His Ser Asn Cys Val Ser Phe Glu Cys Lys Thr Asp Pro Gly Val
        115                 120                 125

Phe Ile Gly Val Lys Asp Asn His Leu Ala Leu Ile Lys Val Asp Ser

```
           130               135               140
Ser Glu Asn Leu Cys Thr Glu Asn Ile Leu Phe Lys Leu Ser Glu Thr
145                   150               155               160

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 3

His His His His His His His His
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 4

His His His His His His
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Glu Asn Leu Tyr Phe Gln Gly
1               5

<210> SEQ ID NO 6
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Gly Trp Ser Cys Ile Ile Leu Phe Leu Val Ala Thr Ala Thr Gly
1               5                   10                  15

Val His Ser

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Gly Gly Gly
1

<210> SEQ ID NO 8
```

-continued

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Gly Gly Gly Ser Gly Gly Gly Gly
1               5

<210> SEQ ID NO 9
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Lys Arg Val Glu Ser Lys Tyr Gly Pro Pro Cys Pro Pro Cys Pro
1               5                   10                  15

Ala Pro Glu Phe Leu Gly Gly Pro Ser Val Phe Leu Phe Pro Pro Lys
                20                  25                  30

Pro Lys Asp Thr Leu Met Ile Ser Arg Thr Pro Glu Val Thr Cys Val
        35                  40                  45

Val Val Asp Val Ser Gln Glu Asp Pro Glu Val Gln Phe Asn Trp Tyr
    50                  55                  60

Val Asp Gly Val Glu Val His Asn Ala Lys Thr Lys Pro Arg Glu Glu
65                  70                  75                  80

Gln Phe Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Gly Leu Pro Ser Ser Ile Glu Lys Thr Ile Ser Lys Ala Lys Gly Gln
        115                 120                 125

Pro Arg Glu Pro Gln Val Tyr Thr Leu Pro Pro Ser Gln Glu Glu Met
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
            165                 170                 175

Tyr Lys Thr Thr Pro Pro Val Leu Asp Ser Asp Gly Ser Phe Phe Leu
            180                 185                 190

Tyr Ser Arg Leu Thr Val Asp Lys Ser Arg Trp Gln Glu Gly Asn Val
        195                 200                 205

Phe Ser Cys Ser Val Met His Glu Ala Leu His Asn His Tyr Thr Gln
    210                 215                 220

Lys Ser Leu Ser Leu Ser Leu Gly Lys
225                 230

<210> SEQ ID NO 10
<211> LENGTH: 176
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10
```

-continued

```
Met Ser His His His His His His His Glu Asn Leu Tyr Phe Gln
1               5                   10                  15

Gly Ser Ile Thr Gly Ile Ser Pro Ile Thr Glu Tyr Leu Ala Ser Leu
            20                  25                  30

Ser Thr Tyr Asn Asp Gln Ser Ile Thr Phe Ala Leu Glu Asp Glu Ser
            35                  40                  45

Tyr Glu Ile Tyr Val Glu Asp Leu Lys Lys Asp Glu Lys Lys Asp Lys
    50                  55                  60

Val Leu Leu Ser Tyr Tyr Glu Ser Gln His Pro Ser Asn Glu Ser Gly
65                  70                  75                  80

Asp Gly Val Asp Gly Lys Met Leu Met Val Thr Leu Ser Pro Thr Lys
            85                  90                  95

Asp Phe Trp Leu His Ala Asn Asn Lys Glu His Ser Val Glu Leu His
            100                 105                 110

Lys Cys Glu Lys Pro Leu Pro Asp Gln Ala Phe Phe Val Leu His Asn
            115                 120                 125

Met His Ser Asn Cys Val Ser Phe Glu Cys Lys Thr Asp Pro Gly Val
            130                 135                 140

Phe Ile Gly Val Lys Asp Asn His Leu Ala Leu Ile Lys Val Asp Ser
145                 150                 155                 160

Ser Glu Asn Leu Cys Thr Glu Asn Ile Leu Phe Lys Leu Ser Glu Thr
                165                 170                 175
```

<210> SEQ ID NO 11
<211> LENGTH: 189
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Met Gly Trp Ser Cys Ile Ile Leu Phe Leu Val Ala Thr Ala Thr Gly
1               5                   10                  15

Val His Ser His His His His His His Gly Gly Gly Gly Ser Ser Ile
            20                  25                  30

Thr Gly Ile Ser Pro Ile Thr Glu Tyr Leu Ala Ser Leu Ser Thr Tyr
            35                  40                  45

Asn Asp Gln Ser Ile Thr Phe Ala Leu Glu Asp Glu Ser Tyr Glu Ile
    50                  55                  60

Tyr Val Glu Asp Leu Lys Lys Asp Glu Lys Lys Asp Lys Val Leu Leu
65                  70                  75                  80

Ser Tyr Tyr Glu Ser Gln His Pro Ser Asn Glu Ser Gly Asp Gly Val
            85                  90                  95

Asp Gly Lys Met Leu Met Val Thr Leu Ser Pro Thr Lys Asp Phe Trp
            100                 105                 110

Leu His Ala Asn Asn Lys Glu His Ser Val Glu Leu His Lys Cys Glu
            115                 120                 125

Lys Pro Leu Pro Asp Gln Ala Phe Phe Val Leu His Asn Met His Ser
            130                 135                 140

Asn Cys Val Ser Phe Glu Cys Lys Thr Asp Pro Gly Val Phe Ile Gly
145                 150                 155                 160

Val Lys Asp Asn His Leu Ala Leu Ile Lys Val Asp Ser Ser Glu Asn
                165                 170                 175

Leu Cys Thr Glu Asn Ile Leu Phe Lys Leu Ser Glu Thr
                180                 185
```

```
<210> SEQ ID NO 12
<211> LENGTH: 421
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Gly Trp Ser Cys Ile Ile Leu Phe Leu Val Ala Thr Ala Thr Gly
1               5                   10                  15

Val His Ser Asp Lys Arg Val Glu Ser Lys Tyr Gly Pro Pro Cys Pro
            20                  25                  30

Pro Cys Pro Ala Pro Glu Phe Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser Gln Glu Asp Pro Glu Val Gln Phe
65                  70                  75                  80

Asn Trp Tyr Val Asp Gly Val Glu Val His Asn Ala Lys Thr Lys Pro
                85                  90                  95

Arg Glu Glu Gln Phe Asn Ser Thr Tyr Arg Val Val Ser Val Leu Thr
            100                 105                 110

Val Leu His Gln Asp Trp Leu Asn Gly Lys Glu Tyr Lys Cys Lys Val
            115                 120                 125

Ser Asn Lys Gly Leu Pro Ser Ser Ile Glu Lys Thr Ile Ser Lys Ala
            130                 135                 140

Lys Gly Gln Pro Arg Glu Pro Gln Val Tyr Thr Leu Pro Pro Ser Gln
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
                180                 185                 190

Glu Asn Asn Tyr Lys Thr Thr Pro Pro Val Leu Asp Ser Asp Gly Ser
            195                 200                 205

Phe Phe Leu Tyr Ser Arg Leu Thr Val Asp Lys Ser Arg Trp Gln Glu
        210                 215                 220

Gly Asn Val Phe Ser Cys Ser Val Met His Glu Ala Leu His Asn His
225                 230                 235                 240

Tyr Thr Gln Lys Ser Leu Ser Leu Ser Leu Gly Lys Gly Gly Gly Gly
                245                 250                 255

Ser Gly Gly Gly Gly Ser Ser Ile Thr Gly Ile Ser Pro Ile Thr Glu
            260                 265                 270

Tyr Leu Ala Ser Leu Ser Thr Tyr Asn Asp Gln Ser Ile Thr Phe Ala
        275                 280                 285

Leu Glu Asp Glu Ser Tyr Glu Ile Tyr Val Glu Asp Leu Lys Lys Asp
        290                 295                 300

Glu Lys Lys Asp Lys Val Leu Leu Ser Tyr Tyr Glu Ser Gln His Pro
305                 310                 315                 320

Ser Asn Glu Ser Gly Asp Gly Val Asp Gly Lys Met Leu Met Val Thr
                325                 330                 335

Leu Ser Pro Thr Lys Asp Phe Trp Leu His Ala Asn Asn Lys Glu His
            340                 345                 350

Ser Val Glu Leu His Lys Cys Glu Lys Pro Leu Pro Asp Gln Ala Phe
```

-continued

```
            355                   360                   365
Phe Val Leu His Asn Met His Ser Asn Cys Val Ser Phe Glu Cys Lys
    370                   375                   380

Thr Asp Pro Gly Val Phe Ile Gly Val Lys Asp Asn His Leu Ala Leu
385                   390                   395                   400

Ile Lys Val Asp Ser Ser Glu Asn Leu Cys Thr Glu Asn Ile Leu Phe
                405                   410                   415

Lys Leu Ser Glu Thr
            420

<210> SEQ ID NO 13
<211> LENGTH: 534
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
atgtcccacc atcaccatca ccaccaccac gaaaatctgt acttccaagg cagcatcacc        60
ggcatcagcc ccatcaccga gtatctggcc tctctgtcca cctacaacga ccagtccatc       120
acattcgctc tggaggacga aagctacgag atctacgtgg aggatctgaa gaaggacgag       180
aagaaggaca aggtgctgct gtcctactac gagtcccagc accctccaa  cgaaagcggc       240 gacggcgtgg atgcaagat  gctgatggtg acactgagcc ccaccaagga cttttggctg       300
cacgccaaca caaggagca  cagcgtggag ctgcacaagt gcgagaaacc tctgcccgac       360
caagccttct tcgtgctgca acatgcac   agcaactgcg tgtccttcga gtgcaagacc       420
gaccccggcg tgttcatcgg cgtgaaggac aaccatctgg ctctgatcaa ggtggacagc       480
tccgagaacc tctgcaccga gaacattctg ttcaagctgt ccgagacctg atga            534

<210> SEQ ID NO 14
<211> LENGTH: 548
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
aagcttatgt cccaccatca ccatcaccac caccacgaaa tctgtactt  ccaaggcagc        60 atcaccggca tcagccccat caccgagtat ctggcctctc tgtccaccta caacgaccag       120
tccatcacat cgctctgga  ggacgaaagc tacgagatct acgtggagga tctgaagaag       180
gacgagaaga aggacaaggt gctgctgtcc tactacgagt cccagcaccc ctccaacgaa       240
agcggcgacg gcgtggatgg caagatgctg atggtgacac tgagcccac  caaggacttt       300 tggctgcacg ccaacaacaa ggagcacagc gtggagctgc acaagtgcga gaaacctctg       360
cccgaccaag ccttcttcgt gctgcacaac atgcacagca actgcgtgtc cttcgagtgc       420
aagaccgacc ccggcgtgtt catcggcgtg aaggacaacc atctggctct gatcaaggtg       480
gacagctccg agaacctctg caccgagaac attctgttca gctgtccga  gacctgatga       540 gcggccgc                                                                548

<210> SEQ ID NO 15
<211> LENGTH: 8
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 15

Ser Ile Ile Asn Phe Glu Lys Leu
1               5
```